United States Patent
Coccia et al.

(10) Patent No.: US 10,881,731 B2
(45) Date of Patent: Jan. 5, 2021

(54) METHODS FOR INDUCING AN IMMUNE RESPONSE

(71) Applicant: GlaxoSmithKline Biologicals SA, Rixensart (BE)

(72) Inventors: Margherita Coccia, Rixensart (BE); Arnauld Michel Didierlaurent, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/471,583

(22) PCT Filed: Dec. 19, 2017

(86) PCT No.: PCT/EP2017/083450
§ 371 (c)(1),
(2) Date: Jun. 20, 2019

(87) PCT Pub. No.: WO2018/114892
PCT Pub. Date: Jun. 28, 2018

(65) Prior Publication Data
US 2020/0000912 A1 Jan. 2, 2020

(30) Foreign Application Priority Data
Dec. 20, 2016 (GB) .................................. 1621686.3

(51) Int. Cl.
*A61K 39/39* (2006.01)
*A61K 39/00* (2006.01)

(52) U.S. Cl.
CPC .......... *A61K 39/39* (2013.01); *A61K 2039/54* (2013.01); *A61K 2039/545* (2013.01); *A61K 2039/55555* (2013.01); *A61K 2039/55572* (2013.01); *A61K 2039/55577* (2013.01)

(58) Field of Classification Search
None
See application file for complete search history.

(56) References Cited

U.S. PATENT DOCUMENTS

| | | | | |
|---|---|---|---|---|
| 7,214,499 B2* | 5/2007 | Finlay | ................. | C07K 14/245 424/241.1 |
| 2008/0319400 A1* | 12/2008 | Thorne, Jr. | ........... | A61M 5/284 604/191 |

FOREIGN PATENT DOCUMENTS

EP 0 761 231 A1 3/1997

OTHER PUBLICATIONS

Coccia et al 2014 Immunology, (Dec. 2014) vol. 143, Supp. Suppl. 2,pp. 61. Abstract No. 459 (Meeting Info: Annual Congress of the British Society for Immunology 2014. Brighton, United Kingdom. Dec. 1, 2014-Dec. 4, 2014. (Year: 2014).*
Margherita Coccia et al: "Cellular and molecular synergy in ASOI-adjuvanted vaccines results in an early IFN[gamma] response promoting vaccine immunogenicity", NPJ Vaccines, vol. 2, No. 1, Dec. 1, 2017, ISSN: 2059-0105.

* cited by examiner

*Primary Examiner* — Padmavathi Baskar
(74) *Attorney, Agent, or Firm* — Birch, Stewart, Kolasch & Birch, LLP

(57) ABSTRACT

The present invention relates to methods for inducing an immune response, in particular methods for adjuvanting the immune response to an antigen comprising the separate administration of a saponin and a TLR4 agonist.

10 Claims, 6 Drawing Sheets
Specification includes a Sequence Listing.

SEQUENCE LISTING

<160> NUMBER OF SEQ ID NOS: 9

<210> SEQ ID NO 1
<211> LENGTH: 424
<212> TYPE: PRT
<213> ORGANISM: Artificial

<220> FEATURE:
<223> OTHER INFORMATION: RTS

<400> SEQUENCE: 1

```
Met Met Ala Pro Asp Pro Asn Ala Asn Pro Asn Ala Asn Pro Asn Ala
1               5                   10                  15

Asn Pro Asn Ala Asn Pro Asn Ala Asn Pro Asn Ala Asn Pro Asn Ala
            20                  25                  30

Asn Pro Asn Ala Asn Pro Asn Ala Asn Pro Asn Ala Asn Pro Asn Ala
        35                  40                  45

Asn Pro Asn Ala Asn Pro Asn Ala Asn Pro Asn Ala Asn Pro Asn Ala
    50                  55                  60

Asn Pro Asn Ala Asn Pro Asn Ala Asn Pro Asn Ala Asn Pro Asn Lys
65                  70                  75                  80

Asn Asn Gln Gly Asn Gly Gln Gly His Asn Met Pro Asn Asp Pro Asn
                85                  90                  95

Arg Asn Val Asp Glu Asn Ala Asn Ala Asn Ser Ala Val Lys Asn Asn
            100                 105                 110

Asn Asn Glu Glu Pro Ser Asp Lys His Ile Lys Glu Tyr Leu Asn Lys
        115                 120                 125

Ile Gln Asn Ser Leu Ser Thr Glu Trp Ser Pro Cys Ser Val Thr Cys
    130                 135                 140

Gly Asn Gly Ile Gln Val Arg Ile Lys Pro Gly Ser Ala Asn Lys Pro
145                 150                 155                 160

Lys Asp Glu Leu Asp Tyr Ala Asn Asp Ile Glu Lys Lys Ile Cys Lys
                165                 170                 175

Met Glu Lys Cys Ser Ser Val Phe Asn Val Val Asn Ser Ser Ile Gly
            180                 185                 190

Leu Gly Pro Val Thr Asn Met Glu Asn Ile Thr Ser Gly Phe Leu Gly
        195                 200                 205

Pro Leu Leu Val Leu Gln Ala Gly Phe Phe Leu Leu Thr Arg Ile Leu
    210                 215                 220

Thr Ile Pro Gln Ser Leu Asp Ser Trp Trp Thr Ser Leu Asn Phe Leu
225                 230                 235                 240

Gly Gly Ser Pro Val Cys Leu Gly Gln Asn Ser Gln Ser Pro Thr Ser
                245                 250                 255

Asn His Ser Pro Thr Ser Cys Pro Pro Ile Cys Pro Gly Tyr Arg Trp
            260                 265                 270

Met Cys Leu Arg Arg Phe Ile Ile Phe Leu Phe Ile Leu Leu Leu Cys
        275                 280                 285

Leu Ile Phe Leu Leu Val Leu Leu Asp Tyr Gln Gly Met Leu Pro Val
    290                 295                 300

Cys Pro Leu Ile Pro Gly Ser Thr Thr Thr Asn Thr Gly Pro Cys Lys
305                 310                 315                 320

Thr Cys Thr Thr Pro Ala Gln Gly Asn Ser Met Phe Pro Ser Cys Cys
                325                 330                 335

Cys Thr Lys Pro Thr Asp Gly Asn Cys Thr Cys Ile Pro Ile Pro Ser
            340                 345                 350

Ser Trp Ala Phe Ala Lys Tyr Leu Trp Glu Trp Ala Ser Val Arg Phe
        355                 360                 365

Ser Trp Leu Ser Leu Leu Val Pro Phe Val Gln Trp Phe Val Gly Leu
    370                 375                 380

Ser Pro Thr Val Trp Leu Ser Ala Ile Trp Met Met Trp Tyr Trp Gly
385                 390                 395                 400
```

```
Pro Ser Leu Tyr Ser Ile Val Ser Pro Phe Ile Pro Leu Leu Pro Ile
            405                 410                 415

Phe Phe Cys Leu Trp Val Tyr Ile
            420

<210> SEQ ID NO 2
<211> LENGTH: 391
<212> TYPE: PRT
<213> ORGANISM: Mycobacterium tuberculosis

<400> SEQUENCE: 2

Met Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Gln Met Trp
            20                  25                  30

Asp Ser Val Ala Ser Asp Leu Phe Ser Ala Ala Ser Ala Phe Gln Ser
            35                  40                  45

Val Val Trp Gly Leu Thr Val Gly Ser Trp Ile Gly Ser Ser Ala Gly
        50                  55                  60

Leu Met Val Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Val Ile Ala
            100                 105                 110

Glu Asn Arg Ala Glu Leu Met Ile Leu Ile Ala Thr Asn Leu Leu Gly
            115                 120                 125

Gln Asn Thr Pro Ala Ile Ala Val Asn Glu Ala Glu Tyr Gly Glu Met
        130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                165                 170                 175

Ser Ala Gly Gly Leu Leu Glu Gln Ala Ala Ala Val Glu Glu Ala Ser
            180                 185                 190

Asp Thr Ala Ala Ala Asn Gln Leu Met Asn Asn Val Pro Gln Ala Leu
        195                 200                 205

Gln Gln Leu Ala Gln Pro Thr Gln Gly Thr Thr Pro Ser Ser Lys Leu
210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
            260                 265                 270

Ala Ala Ala Gln Ala Val Gln Thr Ala Ala Gln Asn Gly Val Arg Ala
        275                 280                 285

Met Ser Ser Leu Gly Ser Ser Leu Gly Ser Ser Gly Leu Gly Gly Gly
    290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
```

```
                    340                 345                 350
Gln Met Leu Gly Gly Leu Pro Val Gly Gln Met Gly Ala Arg Ala Gly
                355                 360                 365

Gly Gly Leu Ser Gly Val Leu Arg Val Pro Arg Pro Tyr Val Met
        370                 375                 380

Pro His Ser Pro Ala Ala Gly
385                 390

<210> SEQ ID NO 3
<211> LENGTH: 323
<212> TYPE: PRT
<213> ORGANISM: Mycobacterium tuberculosis

<400> SEQUENCE: 3

Ala Pro Pro Ala Leu Ser Gln Asp Arg Phe Ala Asp Phe Pro Ala Leu
1               5                   10                  15

Pro Leu Asp Pro Ser Ala Met Val Ala Gln Val Gly Pro Gln Val Val
                20                  25                  30

Asn Ile Asn Thr Lys Leu Gly Tyr Asn Asn Ala Val Gly Ala Gly Thr
            35                  40                  45

Gly Ile Val Ile Asp Pro Asn Gly Val Val Leu Thr Asn Asn His Val
        50                  55                  60

Ile Ala Gly Ala Thr Asp Ile Asn Ala Phe Ser Val Gly Ser Gly Gln
65                  70                  75                  80

Thr Tyr Gly Val Asp Val Val Gly Tyr Asp Arg Thr Gln Asp Val Ala
                85                  90                  95

Val Leu Gln Leu Arg Gly Ala Gly Gly Leu Pro Ser Ala Ala Ile Gly
            100                 105                 110

Gly Gly Val Ala Val Gly Glu Pro Val Val Ala Met Gly Asn Ser Gly
        115                 120                 125

Gly Gln Gly Gly Thr Pro Arg Ala Val Pro Gly Arg Val Val Ala Leu
    130                 135                 140

Gly Gln Thr Val Gln Ala Ser Asp Ser Leu Thr Gly Ala Glu Glu Thr
145                 150                 155                 160

Leu Asn Gly Leu Ile Gln Phe Asp Ala Ala Ile Gln Pro Gly Asp Ser
                165                 170                 175

Gly Gly Pro Val Val Asn Gly Leu Gly Gln Val Val Gly Met Asn Thr
            180                 185                 190

Ala Ala Ser Asp Asn Phe Gln Leu Ser Gln Gly Gly Gln Gly Phe Ala
        195                 200                 205

Ile Pro Ile Gly Gln Ala Met Ala Ile Ala Gly Gln Ile Arg Ser Gly
    210                 215                 220

Gly Gly Ser Pro Thr Val His Ile Gly Pro Thr Ala Phe Leu Gly Leu
225                 230                 235                 240

Gly Val Val Asp Asn Asn Gly Asn Gly Ala Arg Val Gln Arg Val Val
                245                 250                 255

Gly Ser Ala Pro Ala Ala Ser Leu Gly Ile Ser Thr Gly Asp Val Ile
            260                 265                 270

Thr Ala Val Asp Gly Ala Pro Ile Asn Ser Ala Thr Ala Met Ala Asp
        275                 280                 285

Ala Leu Asn Gly His His Pro Gly Asp Val Ile Ser Val Thr Trp Gln
    290                 295                 300

Thr Lys Ser Gly Gly Thr Arg Thr Gly Asn Val Thr Leu Ala Glu Gly
305                 310                 315                 320
```

Pro Pro Ala

<210> SEQ ID NO 4
<211> LENGTH: 723
<212> TYPE: PRT
<213> ORGANISM: Artificial
<220> FEATURE:
<223> OTHER INFORMATION: M72

<400> SEQUENCE: 4

```
Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
        35                  40                  45

Gly Leu Gly Val Val Asp Asn Asn Gly Asn Gly Ala Arg Val Gln Arg
    50                  55                  60

Val Val Gly Ser Ala Pro Ala Ala Ser Leu Gly Ile Ser Thr Gly Asp
65                  70                  75                  80

Val Ile Thr Ala Val Asp Gly Ala Pro Ile Asn Ser Ala Thr Ala Met
                85                  90                  95

Ala Asp Ala Leu Asn Gly His His Pro Gly Asp Val Ile Ser Val Thr
            100                 105                 110

Trp Gln Thr Lys Ser Gly Gly Thr Arg Thr Gly Asn Val Thr Leu Ala
        115                 120                 125

Glu Gly Pro Pro Ala Glu Phe Met Val Asp Phe Gly Ala Leu Pro Pro
    130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
            180                 185                 190

Trp Ile Gly Ser Ser Ala Gly Leu Met Val Ala Ala Ala Ser Pro Tyr
        195                 200                 205

Val Ala Trp Met Ser Val Thr Ala Gly Gln Ala Glu Leu Thr Ala Ala
    210                 215                 220

Gln Val Arg Val Ala Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
                245                 250                 255

Ile Ala Thr Asn Leu Leu Gly Gln Asn Thr Pro Ala Ile Ala Val Asn
            260                 265                 270

Glu Ala Glu Tyr Gly Glu Met Trp Ala Gln Asp Ala Ala Ala Met Phe
        275                 280                 285

Gly Tyr Ala Ala Ala Thr Ala Thr Ala Thr Ala Thr Leu Leu Pro Phe
    290                 295                 300

Glu Glu Ala Pro Glu Met Thr Ser Ala Gly Gly Leu Leu Glu Gln Ala
305                 310                 315                 320

Ala Ala Val Glu Glu Ala Ser Asp Thr Ala Ala Ala Asn Gln Leu Met
                325                 330                 335

Asn Asn Val Pro Gln Ala Leu Gln Gln Leu Ala Gln Pro Thr Gln Gly
            340                 345                 350

Thr Thr Pro Ser Ser Lys Leu Gly Gly Leu Trp Lys Thr Val Ser Pro
```

355                 360                 365
His Arg Ser Pro Ile Ser Asn Met Val Ser Met Ala Asn Asn His Met
            370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Gln Ala Val Gln Thr Ala
                405                 410                 415

Ala Gln Asn Gly Val Arg Ala Met Ser Ser Leu Gly Ser Ser Leu Gly
            420                 425                 430

Ser Ser Gly Leu Gly Gly Gly Val Ala Ala Asn Leu Gly Arg Ala Ala
        435                 440                 445

Ser Val Gly Ser Leu Ser Val Pro Gln Ala Trp Ala Ala Ala Asn Gln
    450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly
                485                 490                 495

Gln Met Gly Ala Arg Ala Gly Gly Leu Ser Gly Val Leu Arg Val
            500                 505                 510

Pro Pro Arg Pro Tyr Val Met Pro His Ser Pro Ala Ala Gly Asp Ile
        515                 520                 525

Ala Pro Pro Ala Leu Ser Gln Asp Arg Phe Ala Asp Phe Pro Ala Leu
    530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
                565                 570                 575

Gly Ile Val Ile Asp Pro Asn Gly Val Val Leu Thr Asn Asn His Val
            580                 585                 590

Ile Ala Gly Ala Thr Asp Ile Asn Ala Phe Ser Val Gly Ser Gly Gln
        595                 600                 605

Thr Tyr Gly Val Asp Val Val Gly Tyr Asp Arg Thr Gln Asp Val Ala
    610                 615                 620

Val Leu Gln Leu Arg Gly Ala Gly Gly Leu Pro Ser Ala Ala Ile Gly
625                 630                 635                 640

Gly Gly Val Ala Val Gly Glu Pro Val Val Ala Met Gly Asn Ser Gly
                645                 650                 655

Gly Gln Gly Gly Thr Pro Arg Ala Val Pro Gly Arg Val Val Ala Leu
            660                 665                 670

Gly Gln Thr Val Gln Ala Ser Asp Ser Leu Thr Gly Ala Glu Glu Thr
        675                 680                 685

Leu Asn Gly Leu Ile Gln Phe Asp Ala Ala Ile Gln Pro Gly Asp Ala
    690                 695                 700

Gly Gly Pro Val Val Asn Gly Leu Gly Gln Val Val Gly Met Asn Thr
705                 710                 715                 720

Ala Ala Ser

<210> SEQ ID NO 5
<211> LENGTH: 725
<212> TYPE: PRT
<213> ORGANISM: Artificial
<220> FEATURE:
<223> OTHER INFORMATION: M72-2His

<400> SEQUENCE: 5

```
Met His His Thr Ala Ala Ser Asp Asn Phe Gln Leu Ser Gln Gly Gly
1               5                   10                  15

Gln Gly Phe Ala Ile Pro Ile Gly Gln Ala Met Ala Ile Ala Gly Gln
            20                  25                  30

Ile Arg Ser Gly Gly Gly Ser Pro Thr Val His Ile Gly Pro Thr Ala
        35                  40                  45

Phe Leu Gly Leu Gly Val Val Asp Asn Asn Gly Asn Gly Ala Arg Val
    50                  55                  60

Gln Arg Val Val Gly Ser Ala Pro Ala Ala Ser Leu Gly Ile Ser Thr
65                  70                  75                  80

Gly Asp Val Ile Thr Ala Val Asp Gly Ala Pro Ile Asn Ser Ala Thr
                85                  90                  95

Ala Met Ala Asp Ala Leu Asn Gly His His Pro Gly Asp Val Ile Ser
            100                 105                 110

Val Thr Trp Gln Thr Lys Ser Gly Gly Thr Arg Thr Gly Asn Val Thr
        115                 120                 125

Leu Ala Glu Gly Pro Pro Ala Glu Phe Met Val Asp Phe Gly Ala Leu
    130                 135                 140

Pro Pro Glu Ile Asn Ser Ala Arg Met Tyr Ala Gly Pro Gly Ser Ala
145                 150                 155                 160

Ser Leu Val Ala Ala Ala Gln Met Trp Asp Ser Val Ala Ser Asp Leu
                165                 170                 175

Phe Ser Ala Ala Ser Ala Phe Gln Ser Val Val Trp Gly Leu Thr Val
            180                 185                 190

Gly Ser Trp Ile Gly Ser Ser Ala Gly Leu Met Val Ala Ala Ala Ser
        195                 200                 205

Pro Tyr Val Ala Trp Met Ser Val Thr Ala Gly Gln Ala Glu Leu Thr
    210                 215                 220

Ala Ala Gln Val Arg Val Ala Ala Ala Tyr Glu Thr Ala Tyr Gly Leu
225                 230                 235                 240

Leu Thr Val Pro Pro Pro Val Ile Ala Glu Asn Arg Ala Glu Leu Met
                245                 250                 255

Ile Leu Ile Ala Thr Asn Leu Leu Gly Gln Asn Thr Pro Ala Ile Ala
            260                 265                 270

Val Asn Glu Ala Glu Tyr Gly Glu Met Trp Ala Gln Asp Ala Ala Ala
        275                 280                 285

Met Phe Gly Tyr Ala Ala Ala Thr Ala Thr Ala Thr Ala Thr Leu Leu
    290                 295                 300

Pro Phe Glu Glu Ala Pro Glu Met Thr Ser Ala Gly Gly Leu Leu Glu
305                 310                 315                 320

Gln Ala Ala Ala Val Glu Glu Ala Ser Asp Thr Ala Ala Ala Asn Gln
                325                 330                 335

Leu Met Asn Asn Val Pro Gln Ala Leu Gln Gln Leu Ala Gln Pro Thr
            340                 345                 350

Gln Gly Thr Thr Pro Ser Ser Lys Leu Gly Gly Leu Trp Lys Thr Val
        355                 360                 365

Ser Pro His Arg Ser Pro Ile Ser Asn Met Val Ser Met Ala Asn Asn
    370                 375                 380

His Met Ser Met Thr Asn Ser Gly Val Ser Met Thr Asn Thr Leu Ser
385                 390                 395                 400

Ser Met Leu Lys Gly Phe Ala Pro Ala Ala Ala Gln Ala Val Gln
                405                 410                 415
```

Thr Ala Ala Gln Asn Gly Val Arg Ala Met Ser Ser Leu Gly Ser Ser
                420                 425                 430

Leu Gly Ser Ser Gly Leu Gly Gly Val Ala Ala Asn Leu Gly Arg
        435                 440                 445

Ala Ala Ser Val Gly Ser Leu Ser Val Pro Gln Ala Trp Ala Ala Ala
    450                 455                 460

Asn Gln Ala Val Thr Pro Ala Arg Ala Leu Pro Leu Thr Ser Leu
465                 470                 475                 480

Thr Ser Ala Ala Glu Arg Gly Pro Gly Gln Met Leu Gly Gly Leu Pro
                485                 490                 495

Val Gly Gln Met Gly Ala Arg Ala Gly Gly Leu Ser Gly Val Leu
            500                 505                 510

Arg Val Pro Pro Arg Pro Tyr Val Met Pro His Ser Pro Ala Ala Gly
            515                 520                 525

Asp Ile Ala Pro Pro Ala Leu Ser Gln Asp Arg Phe Ala Asp Phe Pro
            530                 535                 540

Ala Leu Pro Leu Asp Pro Ser Ala Met Val Ala Gln Val Gly Pro Gln
545                 550                 555                 560

Val Val Asn Ile Asn Thr Lys Leu Gly Tyr Asn Asn Ala Val Gly Ala
                565                 570                 575

Gly Thr Gly Ile Val Ile Asp Pro Asn Gly Val Val Leu Thr Asn Asn
            580                 585                 590

His Val Ile Ala Gly Ala Thr Asp Ile Asn Ala Phe Ser Val Gly Ser
            595                 600                 605

Gly Gln Thr Tyr Gly Val Asp Val Val Gly Tyr Asp Arg Thr Gln Asp
    610                 615                 620

Val Ala Val Leu Gln Leu Arg Gly Ala Gly Gly Leu Pro Ser Ala Ala
625                 630                 635                 640

Ile Gly Gly Gly Val Ala Val Gly Glu Pro Val Val Ala Met Gly Asn
                645                 650                 655

Ser Gly Gly Gln Gly Gly Thr Pro Arg Ala Val Pro Gly Arg Val Val
            660                 665                 670

Ala Leu Gly Gln Thr Val Gln Ala Ser Asp Ser Leu Thr Gly Ala Glu
        675                 680                 685

Glu Thr Leu Asn Gly Leu Ile Gln Phe Asp Ala Ala Ile Gln Pro Gly
    690                 695                 700

Asp Ala Gly Gly Pro Val Val Asn Gly Leu Gly Gln Val Val Gly Met
705                 710                 715                 720

Asn Thr Ala Ala Ser
                725

<210> SEQ ID NO 6
<211> LENGTH: 546
<212> TYPE: PRT
<213> ORGANISM: Varicella zoster

<400> SEQUENCE: 6

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

-continued

```
Val Asn Arg Gly Glu Ser Ser Arg Lys Ala Tyr Asp His Asn Ser Pro
 65                  70                  75                  80

Tyr Ile Trp Pro Arg Asn Asp Tyr Asp Gly Phe Leu Glu Asn Ala His
                 85                  90                  95

Glu His His Gly Val Tyr Asn Gln Gly Arg Gly Ile Asp Ser Gly Glu
                100                 105                 110

Arg Leu Met Gln Pro Thr Gln Met Ser Ala Gln Glu Asp Leu Gly Asp
                115                 120                 125

Asp Thr Gly Ile His Val Ile Pro Thr Leu Asn Gly Asp Asp Arg His
            130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
                180                 185                 190

Gly Val Arg Tyr Thr Glu Thr Trp Ser Phe Leu Pro Ser Leu Thr Cys
            195                 200                 205

Thr Gly Asp Ala Ala Pro Ala Ile Gln His Ile Cys Leu Lys His Thr
210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
            275                 280                 285

Leu Arg Thr Glu Lys Gln Tyr Leu Gly Val Tyr Ile Trp Asn Met Arg
290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
                340                 345                 350

Val Gly Asp Thr Phe Ser Leu Ala Met His Leu Gln Tyr Lys Ile His
            355                 360                 365

Glu Ala Pro Phe Asp Leu Leu Leu Glu Trp Leu Tyr Val Pro Ile Asp
            370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
                420                 425                 430

Glu His Ala Asp Asn Tyr Thr Ala Tyr Cys Leu Gly Ile Ser His Met
            435                 440                 445

Glu Pro Ser Phe Gly Leu Ile Leu His Asp Gly Gly Thr Thr Leu Lys
            450                 455                 460

Phe Val Asp Thr Pro Glu Ser Leu Ser Gly Leu Tyr Val Phe Val Val
465                 470                 475                 480
```

-continued

```
Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Ile Arg Tyr Ala Ala Trp Thr Gly Gly
    530                 535                 540

Leu Ala
545

<210> SEQ ID NO 7
<211> LENGTH: 514
<212> TYPE: PRT
<213> ORGANISM: respiratory syncytial virus

<400> SEQUENCE: 7

Met Glu Leu Leu Ile Leu Lys Thr Asn Ala Ile Thr Ala Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Ser Ala Val Thr Glu Leu Gln Leu Leu
                85                  90                  95

Met Gln Ser Thr Pro Ala Thr Asn Asn Lys Phe Leu Gly Phe Leu Gln
            100                 105                 110

Gly Val Gly Ser Ala Ile Ala Ser Gly Ile Ala Val Ser Lys Val Leu
        115                 120                 125

His Leu Glu Gly Glu Val Asn Lys Ile Lys Ser Ala Leu Leu Ser Thr
    130                 135                 140

Asn Lys Ala Val Val Ser Leu Ser Asn Gly Val Ser Val Leu Thr Ser
145                 150                 155                 160

Lys Val Leu Asp Leu Lys Asn Tyr Ile Asp Lys Gln Leu Leu Pro Ile
                165                 170                 175

Val Asn Lys Gln Ser Cys Ser Ile Ser Asn Ile Glu Thr Val Ile Glu
            180                 185                 190

Phe Gln Gln Lys Asn Asn Arg Leu Leu Glu Ile Thr Arg Glu Phe Ser
        195                 200                 205

Val Asn Ala Gly Val Thr Thr Pro Val Ser Thr Tyr Met Leu Thr Asn
    210                 215                 220

Ser Glu Leu Leu Ser Leu Ile Asn Asp Met Pro Ile Thr Asn Asp Gln
225                 230                 235                 240

Lys Lys Leu Met Ser Asn Asn Val Gln Ile Val Arg Gln Gln Ser Tyr
                245                 250                 255

Ser Ile Met Ser Ile Ile Lys Glu Glu Val Leu Ala Tyr Val Val Gln
            260                 265                 270

Leu Pro Leu Tyr Gly Val Ile Asp Thr Pro Cys Trp Lys Leu His Thr
        275                 280                 285

Ser Pro Leu Cys Thr Thr Asn Thr Lys Glu Gly Ser Asn Ile Cys Leu
    290                 295                 300
```

```
Thr Arg Thr Asp Arg Gly Trp Tyr Cys Asp Asn Ala Gly Ser Val Ser
305                 310                 315                 320

Phe Phe Pro Leu Ala Glu Thr Cys Lys Val Gln Ser Asn Arg Val Phe
                325                 330                 335

Cys Asp Thr Met Asn Ser Leu Thr Leu Pro Ser Glu Val Asn Leu Cys
            340                 345                 350

Asn Ile Asp Ile Phe Asn Pro Lys Tyr Asp Cys Lys Ile Met Thr Ser
        355                 360                 365

Lys Thr Asp Val Ser Ser Val Ile Thr Ser Leu Gly Ala Ile Val
    370                 375                 380

Ser Cys Tyr Gly Lys Thr Lys Cys Thr Ala Ser Asn Lys Asn Arg Gly
385                 390                 395                 400

Ile Ile Lys Thr Phe Ser Asn Gly Cys Asp Tyr Val Ser Asn Lys Gly
                405                 410                 415

Val Asp Thr Val Ser Val Gly Asn Thr Leu Tyr Tyr Val Asn Lys Gln
            420                 425                 430

Glu Gly Lys Ser Leu Tyr Val Lys Gly Glu Pro Ile Ile Asn Phe Tyr
        435                 440                 445

Asp Pro Leu Val Phe Pro Ser Asp Glu Phe Asp Ala Ser Ile Ser Gln
    450                 455                 460

Val Asn Glu Lys Ile Asn Gly Thr Leu Ala Phe Ile Arg Lys Ser Asp
465                 470                 475                 480

Glu Lys Leu His Asn Val Glu Asp Lys Ile Glu Ile Leu Ser Lys
                485                 490                 495

Ile Tyr His Ile Glu Asn Glu Ile Ala Arg Ile Lys Lys Leu Ile Gly
            500                 505                 510

Glu Ala

<210> SEQ ID NO 8
<211> LENGTH: 488
<212> TYPE: PRT
<213> ORGANISM: Human immunodeficiency virus

<400> SEQUENCE: 8

Asn Thr Glu Asp Leu Trp Val Thr Val Tyr Tyr Gly Val Pro Val Trp
1               5                   10                  15

Arg Asp Ala Lys Thr Thr Leu Phe Cys Ala Ser Asp Ala Lys Ala Tyr
                20                  25                  30

Glu Thr Glu Val His Asn Val Trp Ala Thr His Ala Cys Val Pro Thr
            35                  40                  45

Asp Pro Asn Pro Gln Glu Ile Val Leu Gly Asn Val Thr Glu Asn Phe
    50                  55                  60

Asn Met Trp Lys Asn Asp Met Ala Asp Gln Met His Glu Asp Val Ile
65                  70                  75                  80

Ser Leu Trp Asp Gln Ser Leu Lys Pro Cys Val Lys Leu Thr Pro Leu
                85                  90                  95

Cys Val Thr Leu Asn Cys Thr Asp Thr Asn Val Thr Gly Asn Arg Thr
                100                 105                 110

Val Thr Gly Asn Ser Thr Asn Asn Thr Asn Gly Thr Gly Ile Tyr Asn
            115                 120                 125

Ile Glu Glu Met Lys Asn Cys Ser Phe Asn Ala Thr Thr Glu Leu Arg
    130                 135                 140

Asp Lys Lys His Lys Glu Tyr Ala Leu Phe Tyr Arg Leu Asp Ile Val
145                 150                 155                 160
```

```
Pro Leu Asn Glu Asn Ser Asp Asn Phe Thr Tyr Arg Leu Ile Asn Cys
            165                 170                 175

Asn Thr Ser Thr Ile Thr Gln Ala Cys Pro Lys Val Ser Phe Asp Pro
        180                 185                 190

Ile Pro Ile His Tyr Cys Ala Pro Ala Gly Tyr Ala Ile Leu Lys Cys
            195                 200                 205

Asn Asn Lys Thr Phe Asn Gly Thr Gly Pro Cys Tyr Asn Val Ser Thr
210                 215                 220

Val Gln Cys Thr His Gly Ile Lys Pro Val Val Ser Thr Gln Leu Leu
225                 230                 235                 240

Leu Asn Gly Ser Leu Ala Glu Glu Gly Ile Ile Ile Arg Ser Glu Asn
            245                 250                 255

Leu Thr Glu Asn Thr Lys Thr Ile Ile Val His Leu Asn Glu Ser Val
        260                 265                 270

Glu Ile Asn Cys Thr Arg Pro Asn Asn Asn Thr Arg Lys Ser Val Arg
    275                 280                 285

Ile Gly Pro Gly Gln Ala Phe Tyr Ala Thr Asn Asp Val Ile Gly Asn
290                 295                 300

Ile Arg Gln Ala His Cys Asn Ile Ser Thr Asp Arg Trp Asn Lys Thr
305                 310                 315                 320

Leu Gln Gln Val Met Lys Lys Leu Gly Glu His Phe Pro Asn Lys Thr
            325                 330                 335

Ile Gln Phe Lys Pro His Ala Gly Gly Asp Leu Glu Ile Thr Met His
        340                 345                 350

Ser Phe Asn Cys Arg Gly Glu Phe Phe Tyr Cys Asn Thr Ser Asn Leu
    355                 360                 365

Phe Asn Ser Thr Tyr His Ser Asn Asn Gly Thr Tyr Lys Tyr Asn Gly
370                 375                 380

Asn Ser Ser Ser Pro Ile Thr Leu Gln Cys Lys Ile Lys Gln Ile Val
385                 390                 395                 400

Arg Met Trp Gln Gly Val Gly Gln Ala Thr Tyr Ala Pro Pro Ile Ala
            405                 410                 415

Gly Asn Ile Thr Cys Arg Ser Asn Ile Thr Gly Ile Leu Leu Thr Arg
        420                 425                 430

Asp Gly Gly Phe Asn Thr Thr Asn Asn Thr Glu Thr Phe Arg Pro Gly
    435                 440                 445

Gly Gly Asp Met Arg Asp Asn Trp Arg Ser Glu Leu Tyr Lys Tyr Lys
450                 455                 460

Val Val Glu Ile Lys Pro Leu Gly Ile Ala Pro Thr Lys Ala Lys Arg
465                 470                 475                 480

Arg Val Val Gln Arg Glu Lys Arg
            485

<210> SEQ ID NO 9
<211> LENGTH: 469
<212> TYPE: PRT
<213> ORGANISM: Human immunodeficiency virus

<400> SEQUENCE: 9

Ser Trp Val Thr Val Tyr Tyr Gly Val Pro Val Trp Lys Glu Ala Lys
1               5                   10                  15

Thr Thr Leu Phe Cys Ala Ser Asp Ala Lys Ala Tyr Glu Lys Glu Val
            20                  25                  30

His Asn Val Trp Ala Thr His Ala Cys Val Pro Thr Asp Pro Asn Pro
```

```
                35                  40                  45
Gln Glu Met Val Leu Ala Asn Val Thr Glu Asn Phe Asn Met Trp Lys
 50                  55                  60

Asn Asp Met Val Glu Gln Met His Glu Asp Ile Ile Ser Leu Trp Asp
 65                  70                  75                  80

Glu Ser Leu Lys Pro Cys Val Lys Leu Thr Pro Leu Cys Val Thr Leu
                 85                  90                  95

Asn Cys Thr Asn Val Lys Gly Asn Glu Ser Asp Thr Ser Glu Val Met
                100                 105                 110

Lys Asn Cys Ser Phe Lys Ala Thr Thr Glu Leu Lys Asp Lys Lys His
                115                 120                 125

Lys Val His Ala Leu Phe Tyr Lys Leu Asp Val Pro Leu Asn Gly
                130                 135                 140

Asn Ser Ser Ser Gly Glu Tyr Arg Leu Ile Asn Cys Asn Thr Ser
145                 150                 155                 160

Ala Ile Thr Gln Ala Cys Pro Lys Val Ser Phe Asp Pro Ile Pro Leu
                165                 170                 175

His Tyr Cys Ala Pro Ala Gly Phe Ala Ile Leu Lys Cys Asn Asn Lys
                180                 185                 190

Thr Phe Asn Gly Thr Gly Pro Cys Arg Asn Val Ser Thr Val Gln Cys
                195                 200                 205

Thr His Gly Ile Lys Pro Val Ser Thr Gln Leu Leu Leu Asn Gly
                210                 215                 220

Ser Leu Ala Glu Glu Glu Ile Ile Ile Arg Ser Glu Asn Leu Thr Asn
225                 230                 235                 240

Asn Ala Lys Thr Ile Ile Val His Leu Asn Glu Ser Val Asn Ile Val
                245                 250                 255

Cys Thr Arg Pro Asn Asn Asn Thr Arg Lys Ser Ile Arg Ile Gly Pro
                260                 265                 270

Gly Gln Thr Phe Tyr Ala Thr Gly Asp Ile Ile Gly Asn Ile Arg Gln
                275                 280                 285

Ala His Cys Asn Ile Asn Glu Ser Lys Trp Asn Asn Thr Leu Gln Lys
                290                 295                 300

Val Gly Glu Glu Leu Ala Lys His Phe Pro Ser Lys Thr Ile Lys Phe
305                 310                 315                 320

Glu Pro Ser Ser Gly Gly Asp Leu Glu Ile Thr Thr His Ser Phe Asn
                325                 330                 335

Cys Arg Gly Glu Phe Phe Tyr Cys Asn Thr Ser Asp Leu Phe Asn Gly
                340                 345                 350

Thr Tyr Arg Asn Gly Thr Tyr Asn His Thr Gly Arg Ser Ser Asn Gly
                355                 360                 365

Thr Ile Thr Leu Gln Cys Lys Ile Lys Gln Ile Ile Asn Met Trp Gln
                370                 375                 380

Glu Val Gly Arg Ala Ile Tyr Ala Pro Pro Ile Glu Gly Glu Ile Thr
385                 390                 395                 400

Cys Asn Ser Asn Ile Thr Gly Leu Leu Leu Leu Arg Asp Gly Gly Gln
                405                 410                 415

Ser Asn Glu Thr Asn Asp Thr Glu Thr Phe Arg Pro Gly Gly Gly Asp
                420                 425                 430

Met Arg Asp Asn Trp Arg Ser Glu Leu Tyr Lys Tyr Lys Val Val Glu
                435                 440                 445
```

```
Ile Lys Pro Leu Gly Val Ala Pro Thr Glu Ala Lys Arg Arg Val Val
    450                 455                 460

Glu Arg Glu Lys Arg
465
```

METHODS FOR INDUCING AN IMMUNE RESPONSE

This application is a 371 of International Application No. PCT/EP2017/083450, filed 19 Dec. 2017, which claims the benefit of GB Application Serial No. 1621686.3 filed Dec. 20, 2016.

TECHNICAL FIELD

The present invention relates to methods for inducing an immune response, in particular methods for adjuvanting the immune response to an antigen comprising the separate administration of a saponin and a TLR4 agonist.

BACKGROUND OF THE INVENTION

Adjuvants are included in vaccines to improve humoral and cellular immune responses, particularly in the case of poorly immunogenic subunit vaccines. Similar to natural infections by pathogens, adjuvants rely on the activation of the innate immune system to promote long-lasting adaptive immunity. As simultaneous activation of multiple innate immune pathways is a feature of natural infections, adjuvants may combine multiple immunostimulants in order to promote adaptive immune responses to vaccination.

The Adjuvant System 01 (AS01) is a liposome-based adjuvant which contains two immunostimulants, 3-O-desacyl-4'-monophosphoryl lipid A (3D-MPL) and QS-21 (Garcon and Van Mechelen, 2011). The TLR4 agonist 3D-MPL is a non-toxic derivative of the lipopolysaccharide from *Salmonella minnesota*. QS-21 is a natural saponin molecule extracted from the bark of the South American tree *Quillaja saponaria* Molina (Kensil et al., 1991; Ragupathi et al., 2011). AS01 is included in the recently developed malaria vaccine RTS,S (Mosquirix®) and Herpes zoster HZ/su vaccine (Shingrix®), and in multiple candidate vaccines in development against pathogens such as Herpes zoster (HZ/su), human immunodeficiency virus and *Mycobacterium tuberculosis*. During preclinical and clinical evaluation of these candidate vaccines, both antigen-specific antibody and $CD4^+$ T cell immunity were consistently observed. The ability of AS01 to consistently generate cellular immune responses to vaccination sets it apart from other adjuvants that typically mainly promote humoral responses to vaccination (Black et al., 2015; Garcon and Van Mechelen, 2011). Concomitantly, AS01-adjuvanted vaccines have been efficient in promoting immunogenicity and efficacy of vaccination in challenging populations, such as infants (with RTS,S) and the older adults (with HZ/su).

AS01 injection results in rapid and transient activation of innate immunity in animal models. Neutrophils and monocytes are rapidly recruited to the draining lymph node (dLN) upon immunization. Moreover, AS01 induces recruitment and activation of $MHCII^{high}$ dendritic cells (DC), which are necessary for T cell activation (Didierlaurent A. M. et al., 2014). Some data are also available on the mechanism of action of the components of AS01. 3D-MPL signals via TLR4, stimulating NF-κB transcriptional activity and cytokine production and directly activates antigen-presenting cells (APCs) both in humans and in mice (De Becker et al., 2000; Ismaili et al., 2002; Martin et al., 2003; Mata-Haro et al., 2007). QS-21 promotes high antigen-specific antibody responses and CD8+ T-cell responses in mice (Kensil and Kammer, 1998; Newman et al., 1992; Soltysik et al., 1995) and antigen-specific antibody responses in humans (Livingston et al., 1994). Because of its physical properties, it is thought that QS-21 might act as a danger signal in vivo (Lambrecht et al., 2009; Li et al., 2008). Although QS -21 has been shown to activate ASC-NLRP3 inflammasome and subsequent IL-1β/IL-18 release (Marty-Roix, R. et al., 2016), the exact molecular pathways involved in the adjuvant effect of saponins have yet to be clearly defined.

3D-MPL and QS21 have been shown to act synergistically in the induction of immune responses (Coccia et al. 2016). Furthermore, the manner in which both immunostimulants are provided has been shown to be an important factor which influences the quality of the induced responses, with the liposomal presentation of 3D-MPL and QS21 in AS01 providing higher potency than the oil-in-water emulsion based AS02. (Dendouga et al. 2012)

Despite the passage of over twenty years since combinations of TLR4 agonist 3D-MPL and saponin QS21 were first described (see for example international patent application WO96/33739), to date those skilled in the art have only achieved the synergistic benefits of the combination of a TLR4 agonist and saponin through co-formulation of such immunostimulants.

There remains a need for new immunisation approaches which are alternatives or provide benefits over current approaches, being highly efficacious, safe, conveniently formulated, cost-effective, long-lasting and induce a broad spectrum of cross-reactive immune responses.

SUMMARY OF THE INVENTION

It has now surprisingly been found that co-formulation of TLR4 agonist and saponin is not required, a TLR4 agonist and saponin may be administered separately without substantially compromising the synergistic adjuvant effect which has been seen with co-formulation.

Accordingly, there is provided a TLR4 agonist for use as an adjuvant with a saponin, wherein the TLR4 agonist is administered separately from the saponin. Also provided is a saponin for use as an adjuvant with a TLR4 agonist, wherein the saponin is administered separately from the TLR4 agonist.

The present invention additionally provides the use of a TLR4 agonist in the manufacture of an adjuvant for use with a saponin, wherein the TLR4 agonist is administered separately from the saponin. Further, there is provided the use of a saponin in the manufacture of an adjuvant for use with a TLR4 agonist, wherein the saponin is administered separately from the TLR4 agonist.

Also provided is a method for inducing an immune response in a subject using a TLR4 agonist and a saponin, characterised in that the TLR4 agonist and the saponin are administered separately to the subject. There is provided a method for inducing an immune response in a subject using a TLR4 agonist and a saponin, said method comprising the steps:

(i) administering to the subject the TLR4 agonist;

(ii) administering to the subject the saponin;

wherein the steps can be undertaken in either order, and the TLR4 agonist and the saponin are administered separately.

A method for adjuvanting the immune response of a subject to an antigen using a TLR4 agonist and a saponin, characterised in that the TLR4 agonist and the saponin are administered separately to the subject also forms an aspect of the invention. There is provided a method for adjuvanting the immune response of a subject to an antigen using a TLR4 agonist and a saponin, said method comprising the steps:

(i) administering to the subject the TLR4 agonist;
(ii) administering to the subject the saponin;
(iii) administering to the subject the antigen;

wherein the steps can be undertaken in any order, the TLR4 agonist and the saponin are administered separately, and antigen may optionally be co-formulated with the TLR4 agonist, the saponin or co-formulated with each of the TLR4 agonist and saponin.

The present invention also provides a kit comprising: (i) a first composition comprising a TLR4 agonist; and (ii) a second composition comprising a saponin. Antigen may be present in the first or second composition, or in both the first and second compositions.

Kits are provided comprising: (i) a first composition comprising a TLR4 agonist; (ii) a second composition comprising a saponin; and (iii) instructions indicating that the TLR4 agonist and saponin are to be administered separately. Antigen may be present in the first or second composition, or in both the first and second compositions.

The present invention also provides a kit comprising: (i) a first composition comprising a TLR4 agonist; (ii) a second composition comprising a saponin; and (iii) a third composition comprising an antigen.

Kits are provided comprising: (i) a first composition comprising a TLR4 agonist; (ii) a second composition comprising a saponin; (iii) a third composition comprising an antigen; and (iv) instructions indicating that the TLR4 agonist and saponin are to be administered separately.

Additionally provided is a multi-chamber syringe comprising a first compartment and a second compartment, said first compartment comprising a first composition comprising a TLR4 agonist and said second compartment comprising a second composition comprising a saponin, said first and second compositions being administrable to a subject either sequentially or concurrently (though separately). Antigen may be present in the first or second composition, or in both the first and second compositions. Alternatively, the multi-chamber syringe may comprise a third compartment comprising a third composition comprising antigen.

Also provided is a kit comprising: (i) a first syringe containing a composition comprising a TLR4 agonist; and (ii) a second syringe containing a composition comprising a saponin. Antigen may be present in the first or second composition, or in both the first and second compositions.

Further provided is a kit comprising: (i) a first syringe containing a composition comprising a TLR4 agonist; (ii) a second syringe containing a comprising a saponin; and (iii) a third syringe containing a composition comprising an antigen.

To fully obtain the benefits of the present invention, the TLR4 agonist should be administered in a composition which is substantially free of saponin. Additionally, the saponin should be administered in a composition which is substantially free of TLR4 agonist.

DESCRIPTION OF SEQUENCE IDENTIFIERS

Figure 1:
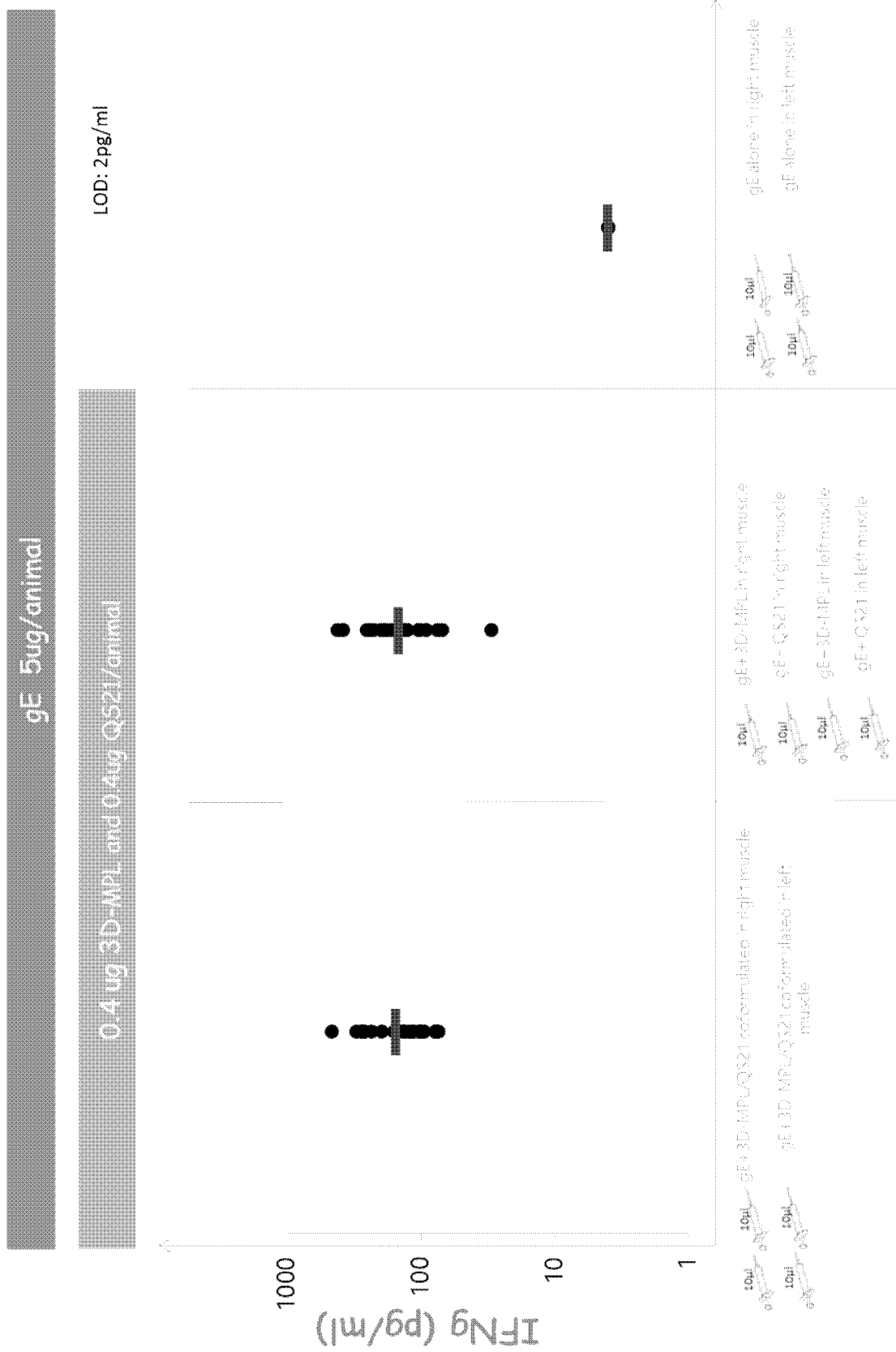
FIG. 1: IFNgamma levels in the dLN 6 hours post-injection following administration of gE antigen alone or gE antigen with separate or co-formulated 3D-MPL and QS21 in mice.

SEQ ID No. 1: RTS polypeptide sequence
SEQ ID No. 2: *M. tuberculosis* H37Rv strain Rv1196 polypeptide sequence
SEQ ID No. 3: *M. tuberculosis* H37Rv strain Rv0125 polypeptide sequence
SEQ ID No. 4: M72 fusion polypeptide sequence
SEQ ID No. 5: M72-2his fusion polypeptide sequence
SEQ ID No. 6: Varicella zoster virus truncated gE polypeptide sequence
SEQ ID No. 7: Conformationally constrained RSV PreF antigen polypeptide sequence
SEQ ID No. 8: HIV TV1 gp120 polypeptide sequence
SEQ ID No. 9: HIV 1086.C gp120 polypeptide sequence

DETAILED DESCRIPTION

It has surprisingly been found that co-formulation of TLR4 agonist and saponin is not required. The TLR4 agonist and saponin may be administered separately without substantially compromising the adjuvant effect. The present invention therefore enables alternative administration approaches based on separate formulation of TLR4 and saponin components, which approaches are advantageous in circumstances such as where co-formulation difficulties exist for a particular vaccine (e.g. stability of the formulation or overcoming other antigen/adjuvant incompatibilities).

Accordingly, there is provided a TLR4 agonist for use as an adjuvant with a saponin, wherein the TLR4 agonist is administered separately from the saponin. Also provided is a saponin for use as an adjuvant with a TLR4 agonist, wherein the saponin is administered separately from the TLR4 agonist.

The present invention additionally provides the use of a TLR4 agonist in the manufacture of an adjuvant for use with a saponin, wherein the TLR4 agonist is administered separately from the saponin. Further, there is provided the use of a saponin in the manufacture of an adjuvant for use with a TLR4 agonist, wherein the saponin is administered separately from the TLR4 agonist.

Also provided is a method for inducing an immune response in a subject using a TLR4 agonist and a saponin, characterised in that the TLR4 agonist and the saponin are administered separately to the subject. There is provided a method for inducing an immune response in a subject using a TLR4 agonist and a saponin, said method comprising the steps:

(i) administering to the subject the TLR4 agonist;
(ii) administering to the subject the saponin;

wherein the steps can be undertaken in either order, the TLR4 agonist and the saponin are administered separately.

A method for adjuvanting the immune response of a subject to an antigen using a TLR4 agonist and a saponin, characterised in that the TLR4 agonist and the saponin are administered separately to the subject also forms an aspect of the invention. There is provided a method for adjuvanting the immune response of a subject to an antigen using a TLR4 agonist and a saponin, said method comprising the steps:

(i) administering to the subject the TLR4 agonist;
(ii) administering to the subject the saponin;
(iii) administering to the subject the antigen;

wherein the steps can be undertaken in any order, the TLR4 agonist and the saponin are administered separately, and antigen may optionally be co-formulated with the TLR4 agonist, the saponin or co-formulated with each of the TLR4 agonist and saponin.

The present invention also provides a kit comprising: (i) a first composition comprising a TLR4 agonist; and (ii) a second composition comprising a saponin. Antigen may be present in the first or second composition, or in both the first and second compositions.

Kits are provided comprising: (i) a first composition comprising a TLR4 agonist; (ii) a second composition comprising a saponin; and (iii) instructions indicating that the TLR4 agonist and saponin are to be administered separately. Antigen may be present in the first or second composition, or in both the first and second compositions.

The present invention also provides a kit comprising: (i) a first composition comprising a TLR4 agonist; (ii) a second composition comprising a saponin; and (iii) a third composition comprising an antigen.

Kits are provided comprising: (i) a first composition comprising a TLR4 agonist; (ii) a second composition comprising a saponin; (iii) a third composition comprising an antigen; and (iv) instructions indicating that the TLR4 agonist and saponin are to be administered separately.

Additionally provided is a multi-chamber syringe comprising a first compartment and a second compartment, said first compartment comprising a first composition comprising a TLR4 agonist and said second compartment comprising a second composition comprising a saponin, said first and second compositions being administrable to a subject either sequentially or concurrently (though separately). Antigen may be present in the first or second composition, or in both the first and second compositions. Alternatively, the multi-chamber syringe may comprise a third compartment comprising a third composition comprising antigen.

Also provided is a kit comprising: (i) a first syringe containing a composition comprising a TLR4 agonist; and (ii) a second syringe containing a composition comprising a saponin. Antigen may be present in the first or second composition, or in both the first and second compositions.

Further provided is a kit comprising: (i) a first syringe containing a composition comprising a TLR4 agonist; (ii) a second syringe containing a comprising a saponin; and (iii) a third syringe containing a composition comprising an antigen.

Definitions

Subject

The methods and uses of the present invention are generally intended for mammalian subjects, in particular human subjects. The subject may be a wild or domesticated animal. Mammalian subjects include for example cats, dogs, pigs, sheep, horses or cattle. In one embodiment the invention, the subject is human.

The subject to be treated using the method of the invention may be of any age.

In one embodiment the subject is a human infant (up to 12 months of age). In one embodiment the subject is a human child (less than 18 years of age). In one embodiment the subject is an adult human (aged 18-59). In one embodiment the subject is an older human (aged 60 or greater).

Separate Administration

The term 'administered separately' excludes co-formulation of TLR4 agonist and saponin, but includes simultaneous administration and sequential administration of individually formulated TLR4 agonist and saponin.

Administration Location

The TLR4 agonist and saponin are desirably administered to locations with sufficient spatial proximity such that their synergistic adjuvant effect is not substantially compromised.

The TLR4 agonist and saponin may be administered via various suitable routes, including parenteral, such as intramuscular or subcutaneous administration. The TLR4 agonist and saponin may be administered via different routes. Suitably the TLR4 agonist and saponin are administered via the same route, in particular intramuscularly.

When antigen is also provided, the antigen, TLR4 agonist and saponin may be administered via different routes. Suitably the TLR4 agonist, saponin and antigen are administered via the same route, in particular intramuscularly.

The TLR4 agonist and saponin are desirably administered to a location draining to the same lymph node, such as to the same limb, in particular to the same muscle.

Suitably the TLR4 agonist and saponin are administered intramuscularly to the same muscle.

In certain embodiments, the TLR4 agonist and saponin are administered to the same location.

If an antigen is also provided, suitably the TLR4 agonist, saponin and antigen are administered to a location draining to the same lymph node, such as to the same limb, in particular to the same muscle and especially the same location.

When antigen is also provided, suitably the TLR4 agonist, saponin and antigen are administered intramuscularly to the same muscle.

The spatial separation of administration locations may be at least 5 mm, such as at least 1 cm. The spatial separation of administration locations may be less than 10 cm, such as less than 5 cm apart.

Administration Timing

The TLR4 agonist and saponin are desirably administered with sufficient temporal proximity such that their synergistic adjuvant effect is not substantially compromised. The TLR4 agonist and saponin may be administered within 6 hours of each other. Suitably the TLR4 agonist and saponin are administered within 2 hours of each other, in particular within 1 hour of each other, such as within 30 minutes and especially within 15 minutes (e.g. within 5 minutes).

If the TLR4 agonist and saponin are administered with a delay, the TLR4 agonist may be administered first and the saponin administered second, alternatively, suitably the saponin is administered first and the TLR4 agonist administered second.

When an antigen is also provided, suitably the TLR4 agonist, saponin and antigen are all administered within 6 hours of each other. Suitably the TLR4 agonist, saponin and antigen are administered within 2 hours of each other, in particular within 1 hour, such as within 30 minutes and especially within 15 minutes (e.g. within 5 minutes).

Desirably, the TLR4 agonist and saponin are administered without intentional delay (accounting for the practicalities of multiple administrations). If an antigen is also provided, suitably the TLR4 agonist, saponin and antigen are administered without intentional delay (accounting for the practicalities of multiple administrations).

The delay between administration of the TLR4 agonist and saponin may be at least 5 seconds, such as 10 seconds, and in particular at least 30 seconds.

Administration Regimes

Approaches for establishing strong and lasting immunity often include addition of repeated vaccination, i.e. boosting an immune response by administration of one or more further doses of antigen. Such further administrations may be performed with the same vaccine (homologous boosting) or with a different vaccine (heterologous boosting).

The present invention may be applied as part of a homologous or heterologous prime/boost regimen, as either the priming or the boosting vaccination.

Administration Outcome

The TLR4 agonist and saponin may be administered separately without substantially compromising the synergistic adjuvant effect which has been seen with co-formulation. Suitably the immunological response observed after a method of the present invention is at least 50% of the response observed with co-formulation, such as at least 60%, suitably at least 70%, especially at least 80% and in particular at least 90%. Desirably, the immunological response observed after a method of the present invention is non-inferior to the response observed with co-formulation.

In one embodiment the observed immune response is innate IFNgamma production (such as described in Example 1). In another embodiment the observed immune response is an antibody response (such as described in Example 2). In a third embodiment the observed immune response is a CD4 T cell response (such as described in Example 2).

TLR4 Agonists

A suitable example of a TLR4 agonist is a lipopolysaccharide, suitably a non-toxic derivative of lipid A, particularly a monophosphoryl lipid A and more particularly 3-de-O-acylated monophoshoryl lipid A (3D-MPL).

3D-MPL is sold under the name 'MPL' by GlaxoSmithKline Biologicals N.A. and is referred throughout the document as 3D-MPL. See, for example, U.S. Pat. Nos. 4,436,727; 4,877,611; 4,866,034 and 4,912,094. 3D-MPL can be produced according to the methods described in GB 2 220 211 A. Chemically it is a mixture of 3-deacylated monophosphoryl lipid A with 4, 5 or 6 acylated chains. In the context of the present invention small particle 3D-MPL may be used to prepare the aqueous adjuvant composition. Small particle 3D-MPL has a particle size such that it may be sterile-filtered through a 0.22 um filter. Such preparations are described in WO94/21292. Suitably, powdered 3D-MPL is used to prepare aqueous adjuvant compositions of use in the present invention.

Other TLR4 agonists which can be used are alkyl glucosaminide phosphates (AGPs) such as those described in WO98/50399 or U.S. Pat. No. 6,303,347 (processes for preparation of AGPs are also described). Other AGPs are as described in U.S. Pat. No. 6,764,840. Some AGPs are TLR4 agonists, and some are TLR4 antagonists.

Other TLR4 agonists which may be of use in the present invention include Glucopyranosyl Lipid Adjuvant (GLA) such as described in WO2008/153541 or WO2009/143457 or the literature articles Coler R N et al. (2011) Development and Characterization of Synthetic Glucopyranosyl Lipid Adjuvant System as a Vaccine Adjuvant. PLoS ONE 6(1): e16333. doi:10.1371/journal.pone.0016333 and Arias M A et al. (2012) Glucopyranosyl Lipid Adjuvant (GLA), a Synthetic TLR4 Agonist, Promotes Potent Systemic and Mucosal Responses to Intranasal Immunization with HIVgp140. PLoS ONE 7(7): e41144. doi:10.1371/journal.pone.0041144. WO2008/153541 or WO2009/143457 are incorporated herein by reference for the purpose of defining TLR4 agonists which may be of use in the present invention.

A TLR4 agonist, such as a lipopolysaccharide, such as 3D-MPL, can be used at amounts between 1 and 100 ug per human dose. 3D-MPL may be used at a level of about 50 ug. Examples of suitable ranges are 40-60 ug, suitably 45-55 ug or 49-51 ug, such as 50 ug. In a further embodiment, the human dose comprises 3D-MPL at a level of about 25 ug. Examples of lower ranges include 20-30 ug, suitably 22-28 ug or 24-26 ug, such as 25 ug. Human doses intended for children may be reduced compared to those intended for an adult (e.g. reduction by 50%).

Suitably the TLR4 agonist of use in the invention is isolated. An "isolated" naturally occurring TLR4 agonist is one that is removed from its original environment. For example, separated from some or all of the coexisting materials in the natural system (e.g. being provided in a form at least 50%, such as at least 80%, in particular at least 90% and especially at least 95% (such as at least 99%) pure w/w.

Saponins

A suitable saponin for use in the present invention is Quil A and its derivatives. Quil A is a saponin preparation isolated from the South American tree *Quillaja saponaria* Molina and was first described as having adjuvant activity by Dalsgaard et al. in 1974 ("Saponin adjuvants", Archiv. für die gesamte Virusforschung, Vol. 44, Springer Verlag, Berlin, p 243-254). Purified fractions of Quil A have been isolated by HPLC which retain adjuvant activity without the toxicity associated with Quil A (see, for example, EP0362279). Fractions of general interest include QS7, QS17, QS18 and QS21, for example QS7 and QS21 (also known as QA7 and QA21). QS21 is a saponin of particular interest.

In certain embodiments of the present invention, the saponin is a derivative of *Quillaja saponaria* Molina quil A, suitably an immunologically active fraction of Quil A, such as QS7, QS17, QS18 or QS21, in particular QS21.

The saponin is optimally provided in a less reactogenic composition where it is quenched with an exogenous sterol, such as cholesterol, and is provided in a liposomal formulation as defined herein. Several particular forms of less reactogenic compositions wherein QS21 is quenched with an exogenous cholesterol exist. The saponin/sterol is presented in a liposomal formulation structure. Methods for obtaining saponin/sterol in a liposomal formulation are described in WO96/33739, in particular Example 1.

A saponin, such as QS21, can be used at amounts between 1 and 100 ug per human dose. QS21 may be used at a level of about 50 ug. Examples of suitable ranges are 40-60 ug, suitably 45-55 ug or 49-51 ug, such as 50 ug. In a further embodiment, the human dose comprises QS21 at a level of about 25 ug. Examples of lower ranges include 20-30 ug, suitably 22-28 ug or 24-26 ug, such as 25 ug. Human doses intended for children may be reduced compared to those intended for an adult (e.g. reduction by 50%).

The weight ratio of TLR4 agonist to saponin is suitably between 1:5 to 5:1, suitably 1:1. For example, where 3D-MPL is used at an amount of 50 ug or 25 ug per dose, then suitably QS21 may also be used at an amount of 50 ug or 25 ug per dose (e.g. human dose).

Suitably the saponin of use in the invention is isolated. An "isolated" naturally occurring saponin is one that is removed from its original environment. For example, separated from some or all of the coexisting materials in the natural system (e.g. being provided in a form at least 50%, such as at least 80%, in particular at least 90% and especially at least 95% (such as at least 99%) pure w/w.

Liposomes

The saponin and/or TLR4 agonist may be formulated with any suitable carrier. The saponin and TLR4 agonist may be formulated with different carriers, or one may be formulated with a carrier and the other not formulated with a carrier.

The saponin is suitably formulated with liposomes. Optionally, the TLR4 agonist and saponin are formulated with liposomes.

Liposome size may vary from 30 nm to several um depending on the phospholipid composition and the method used for their preparation. In particular embodiments of the invention, the liposome size will be in the range of 50 nm to 500 nm and in further embodiments 50 nm to 200 nm. Optimally, the liposomes should be stable and have a diameter of ~100 nm to allow sterilization by filtration.

The term 'liposome' is well known in the art and defines a general category of vesicles which comprise one or more lipid bilayers surrounding an aqueous space. Liposomes thus consist of one or more lipid and/or phospholipid bilayers and can contain other molecules, such as proteins or carbohydrates, in their structure. Because both lipid and aqueous phases are present, liposomes can encapsulate or entrap water-soluble material, lipid-soluble material, and/or amphiphilic compounds.

As used herein, a 'neutral liposome based adjuvant' means the adjuvant comprises neutral liposomes for the presentation of the immune-potentiating agents included.

Structural integrity of the liposomes may be assessed by methods such as dynamic light scattering (DLS) measuring the size and polydispersity of the liposomes, or, by electron microscopy for analysis of the structure of the liposomes. In one embodiment the average particle size (by photon correlation spectroscopy) is between 95 and 120 nm, and/or, the polydispersity index (by photon correlation spectroscopy) is not more than 0.2. In another embodiment the average particle size (by photon correlation spectroscopy) is between 95 and 120 nm, and/or, the polydispersity index (by photon correlation spectroscopy) is not more than 0.3.

The liposomes intended for the present invention may contain a neutral lipid or consist essentially of neutral lipid. By "neutral lipid" is understood that the overall net charge of the lipid is (approximately) zero. The lipid may therefore be non-ionic overall or may be zwitterionic. In one embodiment the liposomes comprise a zwitterionic lipid. Examples of suitable lipids are phospholipids such as phosphatidylcholine species. In one embodiment the liposomes contain phosphatidylcholine as a liposome forming lipid which is suitably non-crystalline at room temperature. Examples of such non-crystalline phosphatidylcholine lipids include egg yolk phosphatidylcholine, dioleoyl phosphatidylcholine (DOPC) or dilauryl phosphatidylcholine (DLPC). In a particular embodiment, the liposomes of the present invention contain DOPC, or, consist essentially of DOPC. The liposomes may also contain a limited amount of a charged lipid which increases the stability of the liposome-saponin structure for liposomes composed of saturated lipids. In these cases the amount of charged lipid is suitably 1-20% w/w, preferably 5-10% w/w of the liposome composition. Suitable examples of such charged lipids include phosphatidylglycerol and phosphatidylserine. Suitably, the neutral liposomes will contain less than 5% w/w charged lipid, such as less than 3% w/w or less than 1% w/w.

The liposomes intended for the present invention may further comprise a sterol. Suitable sterols include β-sitosterol, stigmasterol, ergosterol, ergocalciferol and cholesterol. In one particular embodiment, the liposomal formulation comprises cholesterol as sterol. These sterols are well known in the art, for example cholesterol is disclosed in the Merck Index, 11th Edn., page 341, as a naturally occurring sterol found in animal fat. The ratio of sterol to phospholipid is 1-50% (mol/mol), suitably 20-25%.

The ratio of saponin:sterol will typically be in the order of 1:100 to 1:1 (w/w), suitably between 1:10 to 1:1 (w/w), and preferably 1:5 to 1:1 (w/w). Suitably excess sterol is present, the ratio of saponin:sterol being at least 1:2 (w/w). In one embodiment, the ratio of saponin:sterol is 1:5 (w/w). In one embodiment, the sterol is cholesterol.

The amount of liposome (weight of lipid and sterol) will typically be in the range of 0.1 mg to 10 mg per human dose of a composition, in particular 0.5 mg to 2 mg per human dose of a composition.

In a particularly suitable embodiment, liposomes used in the invention comprise (such as consist essentially of) DOPC and a sterol, in particular cholesterol. Thus, in a particular embodiment, a composition used in the invention comprises QS21 in the form of a liposome, wherein said liposome comprises DOPC and a sterol, in particular cholesterol.

If the TLR4 agonist is formulated with liposomes, these may be the same as or different to the liposomes used with the saponin. Consequently, the TLR4 agonist (such as 3D-MPL) may be formulated with liposomes comprising DOPC and a sterol, in particular cholesterol.

Antigen

The compositions, kits and methods of the present invention may include an immunogen or antigen. In some embodiments the compositions, kits and methods of the present invention may include a polynucleotide encoding the immunogen or antigen.

By the term immunogen is meant a polypeptide which is capable of eliciting an immune response. Suitably the immunogen is an antigen which comprises at least one B or T cell epitope. The elicited immune response may be an antigen specific B cell response, which produces neutralizing antibodies. The elicited immune response may be an antigen specific T cell response, which may be a systemic and/or a local response. The antigen specific T cell response may comprise a CD4+ T cell response, such as a response involving CD4+ T cells expressing a plurality of cytokines, e.g. IFNgamma, TNFalpha and/or IL2. Alternatively, or additionally, the antigen specific T cell response comprises a CD8+ T cell response, such as a response involving CD8+ T cells expressing a plurality of cytokines, e.g., IFNgamma, TNFalpha and/or IL2.

The antigen may be derived (such as obtained from) from a human or non-human pathogen including, e.g., bacteria, fungi, parasitic microorganisms or multicellular parasites which infect human and non-human vertebrates, or from a cancer cell or tumor cell.

In one embodiment the antigen is a recombinant protein, such as a recombinant prokaryotic protein.

In one embodiment, the antigen is derived from *Plasmodium* spp. (such as *Plasmodium falciparum*), *Mycobacterium* spp. (such as *Mycobacterium tuberculosis* (TB)), Varicella Zoster Virus (VZV), human respiratory syncytial virus, Human Immunodeficiency Virus (HIV), *Moraxella* spp. (such as *Moraxella catarrhalis*) or nontypable *Haemophilus influenzae* (ntHi).

The antigen may comprise or consist of preparations derived from parasites that cause malaria such as *Plasmodium falciparum* or *Plasmodium vivax*.

In one embodiment, the antigen may be the *Plasmodium falciparum* circumsporozoite (CS) protein or a variant thereof. A suitable variant of the CS protein may be a variant wherein parts of the CS protein are in the form of a hybrid protein with the surface antigen S from hepatitis B (HBsAg). The CS variant antigen may e.g. be in the form of a hybrid protein comprising substantially all the C-terminal portion of the CS protein, four or more tandem repeats of the CS protein immunodominant region, and HBsAg. The hybrid protein may comprise a sequence which contains at least 160 amino acids and which is substantially homologous to the C-terminal portion of the CS protein, but devoid of the hydrophobic anchor sequence. The CS protein may be devoid of the last 12 amino-acids from the C terminal. Further, it may contain 4 or more e.g. 10 or more Asn-Ala-Asn-Pro tetrapeptide (NANP) repeat motifs.

The hybrid protein for use in the invention may be a protein which comprises a portion of the CS protein of *P. falciparum* substantially as corresponding to amino acids 207-395 of *P. falciparum* clone 3D7, derived from the strain NF54 fused in frame via a linear linker to the N-terminus of HBsAg. The linker may comprise a portion of preS2 from HBsAg. CS constructs suitable for use in the present invention are outlined in WO93/10152, which granted in the US as U.S. Pat. Nos. 5,928,902 and 6,169,171, both of which are incorporated by reference for the purpose of describing suitable proteins for use in the present invention.

A particular hybrid protein for use in the invention is the hybrid protein known as RTS (SEQ ID No. 1, also described in WO2015/150568, WO93/10152 (wherein it is denoted RTS*) and in WO98/05355, which consists of:

a methionine residue
three amino acid residues, Met Ala Pro
a stretch of 189 amino acids representing amino acids 207 to 395 of the CS protein of *P. falciparum* strain 3D7
an glycine residue
four amino acid residues, Pro Val Thr Asn, representing the four carboxy terminal residues of the hepatitis B virus (adw serotype) preS2 protein, and
a stretch of 226 amino acids, encoded by nucleotides 1653 to 2330, and specifying the S protein of hepatitis B virus (adw serotype).

RTS may be in the form of RTS,S mixed particles. RTS,S particles comprise two polypeptides, RTS and S, that may be synthesized simultaneously and spontaneously form composite particulate structures (RTS,S).

The antigen may comprise or consist of preparations derived from *Mycobacterium* spp., such as *Mycobacterium bovis* or *Mycobacterium tuberculosis*, in particular *Mycobacterium tuberculosis*.

Antigens of interest in the field of tuberculosis include Rv1196 and Rv0125. Rv1196 (described, for example, by the name Mtb39a in Dillon et al Infection and Immunity 1999 67(6): 2941-2950) is highly conserved, with 100% sequence identity across H37Rv, C, Haarlem, CDC1551, 94-M4241A, 98-R6041NH-RIF-EM, KZN605, KZN1435, KZN4207, KZNR506 strains, the F11 strain having a single point mutation Q30K (most other clinical isolates have in excess of 90% identity to H37Rv). Rv0125 (described, for example, by the name Mtb32a in Skeiky et al Infection and Immunity 1999 67(8): 3998-4007) is also highly conserved, with 100% sequence identity across many strains. Full length Rv0125 includes an N-terminal signal sequence which is cleaved to provide the mature protein.

In one embodiment the antigen is derived from Rv1196, such as comprise, such as consist of, a sequence having at least 70% identity to SEQ ID No: 2, such as at least 80%, in particular at least 90%, especially at least 95%, for example at least 98%, such as at least 99%. Typical Rv1196 related antigens will comprise (such as consist of) a derivative of SEQ ID No: 2 having a small number of deletions, insertions and/or substitutions. Examples are those having deletions of up to 5 residues at 0-5 locations, insertions of up to 5 residues at 0-5 five locations and substitution of up to 20 residues. Other derivatives of Rv1196 are those comprising (such as consisting of) a fragment of SEQ ID No: 2 which is at least 200 amino acids in length, such as at least 250 amino acids in length, in particular at least 300 amino acids in length, especially at least 350 amino acids in length.

In one embodiment the antigen is derived from Rv0125, such as comprise, such as consist of, a sequence having at least 70% identity to SEQ ID No: 3, such as at least 80%, in particular at least 90%, especially at least 95%, for example at least 98%, such as at least 99%. Typical Rv0125 related antigens will comprise (such as consist of) a derivative of SEQ ID No: 3 having a small number of deletions, insertions and/or substitutions. Examples are those having deletions of up to 5 residues at 0-5 locations, insertions of up to 5 residues at 0-5 five locations and substitution of up to 20 residues. Other derivatives of Rv0125 are those comprising (such as consisting of) a fragment of SEQ ID No: 3 which is at least 150 amino acids in length, such as at least 200 amino acids in length, in particular at least 250 amino acids in length, especially at least 300 amino acids in length. Particular derivatives of Rv0125 are those comprising (such as consisting of) the fragment of SEQ ID No: 3 corresponding to residues 1-195 of SEQ ID No: 3. Further immunogenic derivatives of Rv0125 are those comprising (such as consisting of) the fragment of SEQ ID No: 3 corresponding to residues 192-323 of SEQ ID No: 3. Particularly preferred Rv0125 related antigens are derivatives of SEQ ID No: 3 wherein at least one (for example one, two or even all three) of the catalytic triad have been substituted or deleted, such that the protease activity has been reduced and the protein more easily produced—the catalytic serine residue may be deleted or substituted (e.g. substituted with alanine) and/or the catalytic histidine residue may be deleted or substituted and/or substituted the catalytic aspartic acid residue may be deleted or substituted. Especially of interest are derivatives of SEQ ID No: 3 wherein the catalytic serine residue has been substituted (e.g. substituted with alanine). Also of interest are Rv0125 related antigens which comprise, such as consist of, a sequence having at least 70% identity to SEQ ID No: 3, such as at least 80%, in particular at least 90%, especially at least 95%, for example at least 98%, such as at least 99% and wherein at least one of the catalytic triad have been substituted or deleted or those comprising, such as consisting of, a fragment of SEQ ID No: 3 which is at least 150 amino acids in length, such as at least 200 amino acids in length, in particular at least 250 amino acids in length, especially at least 300 amino acids in length and wherein at least one of the catalytic triad have been substituted or deleted. Further immunogenic derivatives of Rv0125 are those comprising (such as consisting of) the fragment of SEQ ID No: 3 corresponding to residues 192-323 of SEQ ID No: 3 wherein at least one (for example one, two or even all three) of the catalytic triad have been substituted or deleted. Particular immunogenic derivatives of Rv0125 are those comprising (such as consisting of) the fragment of SEQ ID No: 3 corresponding to residues 1-195 of SEQ ID No: 3 wherein the catalytic serine residue (position 176 of SEQ ID No: 3) has been substituted (e.g. substituted with alanine).

Suitably the antigen will comprise, such as consist of, a sequence having at least 70% identity to SEQ ID No. 4, such as at least 80%, in particular at least 90%, especially at least 95%, such as at least 98%, for example at least 99%. Typical M72 related antigens will comprise, such as consist of, a derivative of SEQ ID No: 4 having a small number of deletions, insertions and/or substitutions. Examples are those having deletions of up to 5 residues at 0-5 locations, insertions of up to 5 residues at 0-5 five locations and substitution of up to 20 residues. Other derivatives of M72 are those comprising, such as consisting of, a fragment of SEQ ID No: 4 which is at least 450 amino acids in length, such as at least 500 amino acids in length, such as at least 550 amino acids in length, such as at least 600 amino acids in length, such as at least 650 amino acids in length or at least 700 amino acids in length. As M72 is a fusion protein derived from the two individual antigens Rv0125 and Rv1196, any fragment of at least 450 residues will comprise a plurality of epitopes from the full length sequence (Skeiky et al J. Immunol. 2004 172:7618-7628; Skeiky Infect. Immun. 1999 67(8):3998-4007; Dillon Infect. Immun. 1999 67(6):2941-2950).

M72 related antigen will comprise, such as consist of, a sequence having at least 70% identity to SEQ ID No. 4, such as at least 80%, in particular at least 90%, especially at least 95%, such as at least 98%, for example at least 99%.

Typical M72 related antigens will comprise, such as consist of, a derivative of SEQ ID No: 4 having a small number of deletions, insertions and/or substitutions. Examples are those having deletions of up to 5 residues at 0-5 locations, insertions of up to 5 residues at 0-5 five locations and substitution of up to 20 residues.

In particular embodiments the M72 related antigen will comprise residues 2-723 of SEQ ID No. 4, for example comprise (or consist of) SEQ ID No. 4 or comprise (or consist) of SEQ ID No. 5.

A further antigen that may be employed in accordance with the present invention is the tuberculosis antigen Rv1753 and variants thereof, such as described in WO2010010180, for example a Rv1753 sequence selected from Seq ID Nos: 1 and 2-7 of WO2010010180, in particular Seq ID No: 1. Another antigen of interest in the field of tuberculosis is Rv2386 and variants thereof, such as described in WO2010010179, for example a Rv2386 sequence selected from Seq ID Nos: 1 and 2-7 of WO2010010179, in particular Seq ID No: 1. Other antigens of interest in the field of tuberculosis include Rv3616 and variants thereof, such as described in WO2011092253, for example a natural Rv3616 sequence selected from Seq ID Nos: 1 and 2-7 of WO2011092253 or a modified Rv3616 sequence such as those selected from Seq ID Nos: 161 to 169, 179 and 180 of WO2011092253, in particular Seq ID No: 167. An additional antigen of interest is HBHA, such as described in WO97044463, WO03044048 and WO2010149657. The aforementioned patent applications WO2010010180, WO2010010179, WO2011092253, WO97044463, WO03044048 and WO2010149657 are incorporated herein by reference in their entirety for the purpose of defining antigens which may be of use in the present invention.

Other antigens of interest are those comprising (or consisting of): Rv1174, also known as DPV, such as described in SEQ ID No 8 of WO2010010177; Rv1793, also known as MTI or Mtb9.9, such as described in SEQ ID No 10 of WO2010010177; Rv2087, also known as MSL or Mtb9.8, such as described in SEQ ID No 9 of WO2010010177; Rv3616, also known as HTCC1 or Mtb40, such as described in SEQ ID Nos 1 and 2-7 WO2010010177 or SEQ ID Nos 161-169, 179 or 180 of WO2011092253; and/or Rv3874, also known as CFP10 or Tb38.1, such as described in SEQ ID No 9 of WO2010010177; or an immunogenic portion (such as at least 20, 50, 75 or 100 residues therefrom) or variant thereof (such as having at least 70%, 80%, 90% or 95% identity thereto). (WO2010010177 and WO2011092253 are incorporated herein by reference in their entirety for the purpose of defining antigens which may be of use in the present invention).

Tuberculosis antigens are most suitably utilised in the form of a polypeptide, but may alternatively be provided in the form of a polynucleotide encoding said polypeptide.

A further antigen that may be employed in accordance with the present invention is derived from Varicella zoster virus (VZV). The VZV antigen for use in the invention may be any suitable VZV antigen or immunogenic derivative thereof, suitably being a purified VZV antigen.

In one embodiment, the VZV antigen is the VZV glycoprotein gE (also known as gp1) or immunogenic derivative hereof. The wild type or full length gE protein consists of 623 amino acids comprising a signal peptide, the main part of the protein, a hydrophobic anchor region (residues 546-558) and a C-terminal tail. In one aspect, a gE C-terminal truncate (also referred to truncated gE or gE truncate) is used whereby the truncation removes 4 to 20 percent of the total amino acid residues at the carboxy terminal end. In a further aspect, the truncated gE lacks the carboxy terminal anchor region (suitably approximately amino acids 547-623 of the wild type sequence). In a further aspect gE is a truncated gE having the sequence of SEQ ID NO. 6.

The gE antigen, anchorless derivatives thereof (which are also immunogenic derivatives) and production thereof is described in EP0405867 and references therein [see also Vafai A., Antibody binding sites on truncated forms of varicalla-zoster virus gp1(gE) glycoprotein, Vaccine 1994 12:1265-9]. EP192902 also describes gE and production thereof. Truncated gE is also described by Haumont et al. Virus Research (1996) vol 40, p 199-204, herein incorporated fully by reference. An adjuvanted VZV gE composition suitable for use in accordance of the present invention is described in WO2006/094756, i.e. a carboxyterminal truncated VZV gE in combination with adjuvant comprising QS21, 3D-MPL and liposomes further containing cholesterol. Leroux-Roels I. et al. (J. Infect. Dis. 2012,206: 1280-1290) reported on a phase I/II clinical trial evaluating the adjuvanted VZV truncated gE subunit vaccine.

The antigen may comprise or consist of preparations derived from human respiratory syncytial virus (RSV). In certain favorable embodiments, a polypeptide antigen is an F protein polypeptide antigen from RSV. Particularly suitable as a polypeptide antigen component in the context of the are conformationally constrained F polypeptide antigens. Conformationally constrained F proteins have previously been described in both the prefusion (PreF) and postfusion (PostF) conformations. Such conformationally constrained F proteins typically comprise an engineered RSV F protein ectodomain. An F protein ectodomain polypeptide is a portion of the RSV F protein that includes all or a portion of the extracellular domain of the RSV F protein and lacks a functional (e.g., by deletion or substitution) transmembrane domain, which can be expressed, e.g., in soluble (not attached to a membrane) form in cell culture.

Exemplary F protein antigens conformationally constrained in the prefusion conformation have been described in the art and are disclosed in detail in e.g., U.S. Pat. No. 8,563,002 (WO2009079796); US Published patent application No. US2012/0093847 (WO2010/149745); US2011/0305727 (WO2011/008974); US2014/0141037, WO2012/

158613 and WO2014/160463 each of which is incorporated herein by reference for the purpose of illustrating prefusion F polypeptides (and nucleic acids), and methods of their production. Typically, the antigen is in the form of a trimer of polypeptides. Additional publications providing examples of F proteins in the prefusion conformation include: McLellan et al., Science, Vol. 340: 1113-1117; McLellan et al., Science, Vol 342: 592-598, and Rigter et al., PLOS One, Vol. 8: e71072, each of which can also be used in the context of the immunogenic combinations disclosed herein.

For example, an F protein polypeptide stabilized in the prefusion conformation typically includes an ectodomain of an F protein (e.g., a soluble F protein polypeptide) comprising at least one modification that stabilized the prefusion conformation of the F protein. For example, the modification can be selected from an addition of a trimerization domain (typically to the C terminal end), deletion of one or more of the furin cleavage sites (at amino acids ~105-109 and ~133-136), a deletion of the pep27 domain, substitution or addition of a hydrophilic amino acid in a hydrophobic domain (e.g., HRA and/or HRB). In an embodiment, the conformationally constrained PreF antigen comprises an F2 domain (e.g., amino acids 1-105) and an F1 domain (e.g., amino acids 137-516) of an RSV F protein polypeptide with no intervening furin cleavage site wherein the polypeptide further comprises a heterologous trimerization domain positioned C-terminal to the F1 domain. Optionally, the PreF antigen also comprises a modification that alters glycosylation (e.g., increases glycosylation), such as a substitution of one or more amino acids at positions corresponding to amino acids ~500-502 of an RSV F protein. When an oligomerization sequence is present, it is preferably a trimerization sequence. Suitable oligomerization sequences are well known in the art and include, for example, the coiled coil of the yeast GCN4 leucine zipper protein, trimerizing sequence from bacteriophage T4 fibritin ("foldon"), and the trimer domain of influenza HA. Additionally or alternatively, the F polypeptide conformationally constrained in the prefusion conformation can include at least two introduced cysteine residues, which are in close proximity to one another and form a disulfide bond that stabilizes the prefusion RSV F polypeptide. For example, the two cysteines can be within about 10 Å of each other. For example, cysteines can be introduced at positions 165 and 296 or at positions 155 and 290. An exemplary PreF antigen is represented by SEQ ID NO:7.

The antigen may comprise or consist of preparations derived from HIV. The antigen may be a HIV protein such as a HIV envelope protein. For example, the antigen may be a HIV envelope gp120 polypeptide or an immunogenic fragment thereof.

One suitable antigen is the HIV clade B gp120 polypeptide of SEQ ID NO: 8 of the published application WO 2008/107370 (or an immunogenic fragment of this polypeptide). SEQ ID NO: 8 of WO 2008/107370 is incorporated by reference into this application.

Suitable antigens also include a polypeptide comprising the V1V2 region of SEQ ID NO: 1 of the published application WO 2015/036061, or an immunogenic derivative or fragment of the V1V2 region of SEQ ID NO: 1. In addition, a polypeptide comprising the V1V2 region of SEQ ID NO: 5 of WO 2015/036061 or an immunogenic derivative or fragment of the V1V2 region of SEQ ID NO: 5 may be used as a suitable antigen. SEQ ID NO: 1 and SEQ ID NO: 5 of WO2015/036061 are incorporated by reference.

In another embodiment, the antigen may comprise two or more different HIV envelope gp120 polypeptide antigens (or immunogenic fragments of these polypeptides). Suitable antigens include the and HIV clade C gp120 polypeptide antigens including TV1 gp120 (SEQ ID No: 8) and 1086.C gp120 (SEQ ID No: 9).

Other suitable HIV antigens include Nef, Gag and Pol HIV proteins and immunogenic fragments thereof.

The composition may comprise non-typeable *Haemophilus influenzae* antigen(s) for example selected from: Fimbrin protein [(U.S. Pat. No. 5,766,608—Ohio State Research Foundation)] and fusions comprising peptides therefrom [e.g. LB1(f) peptide fusions; U.S. Pat. No. 5,843,464 (OSU) or WO 99/64067]; OMP26 [WO 97/01638 (Cortecs)]; P6 [EP 281673 (State University of New York)]; TbpA and/or TbpB; Hia; Hsf; Hin47; Hif; Hmw1; Hmw2; Hmw3; Hmw4; Hap; D15 (WO 94/12641); protein D (EP 594610); P2; and P5 (WO 94/26304); protein E (WO07/084053) and/or PilA (WO05/063802). The composition may comprise *Moraxella catarrhalis* protein antigen(s), for example selected from: OMP106 [WO 97/41731 (Antex) & WO 96/34960 (PMC)]; OMP21; LbpA &/or LbpB [WO 98/55606 (PMC)]; TbpA &/or TbpB [WO 97/13785 & WO 97/32980 (PMC)]; CopB [Helminen M E, et al. (1993) Infect. Immun. 61:2003-2010]; UspA1 and/or UspA2 [WO 93/03761 (University of Texas)]; OmpCD; HasR (PCT/EP99/03824); PilQ (PCT/EP99/03823); OMP85 (PCT/EP00/01468); lipo06 (GB 9917977.2); lipo10 (GB 9918208.1); lipo11 (GB 9918302.2); lipo18 (GB 9918038.2); P6 (PCT/EP99/03038); D15 (PCT/EP99/03822); OmplAl (PCT/EP99/06781); Hly3 (PCT/EP99/03257); and OmpE.

In an embodiment, the composition may comprise non-typeable *H. influenzae* (NTHi) protein antigen(s) and/or *M. catarrhalis* protein antigen(s). The composition may comprise Protein D (PD) from *H. influenzae*. Protein D may be as described in WO91/18926. The composition may further comprise Protein E (PE) and/or Pilin A (PilA) from H. *Influenzae*. Protein E and Pilin A may be as described in WO2012/139225. Protein E and Pilin A may be presented as a fusion protein; for example LVL735 as described in WO2012/139225. For example, the composition may comprise three NTHi antigens (PD, PE and PilA, with the two last ones combined as a PEPilA fusion protein). The composition may further comprise UspA2 from *M. catarrhalis*. UspA2 may be as described in WO2015125118, for example MC-009 ((M)(UspA2 31-564)(HH)) described in WO2015125118. For example, the composition may comprise three NTHi antigens (PD, PE and PilA, with the two last ones combined as a PEPilA fusion protein) and one *M. catarrhalis* antigen (UspA2).

A plurality of antigens may be provided. For example, a plurality of antigens may be provided to strengthen the elicited immune response (e.g. to ensure strong protection), a plurality of antigens may be provided to broaden the immune response (e.g. to ensure protection against a range of pathogen strains or in a large proportion of a subject population) or a plurality of antigens may be provided to currently elicit immune responses in respect of a number of disorders (thereby simplifying administration protocols). Where a plurality of antigens are provided, these may be as distinct proteins or may be in the form of one or more fusion proteins.

Antigens may be provided separately from the TLR4 agonist and saponin or the antigens may be provided in co-formulation with the TLR4 agonist, saponin or with the TLR4 agonist and also with the saponin. Where a plurality of antigens are provided, some or all of these may be provided separately from the TLR4 agonist and saponin or some or all may be provided in a co-formulation with the TLR4 agonist, saponin or with the TLR4 agonist and also with the saponin. Optionally, a different antigen or antigens may be co-formulated with the TLR4 agonist from those antigen or antigens co-formulated with the saponin.

Antigen may be provided in an amount of 0.1 to 100 ug per human dose.

Further Excipients

The TLR4 agonist, saponin and (as appropriate) the antigen are suitably provided in the form of liquid preparations which are substantially aqueous.

Suitably, the compositions used in the present invention have a human dose volume of between 0.05 ml and 1 ml, such as between 0.1 and 0.5 ml, in particular a dose volume of about 0.5 ml, or 0.7 ml. The volumes of the compositions used may depend on the delivery route and location, with smaller doses being given by the intradermal route or if both the TLR4 agonist and saponin are delivered at the same location.

In a further embodiment, a buffer is added to the composition. The pH of a liquid preparation is adjusted in view of the components of the composition and necessary suitability for administration to the subject. Suitably, the pH of a liquid mixture is at least 4, at least 5, at least 5.5, at least 5.8, at least 6. The pH of the liquid mixture may be less than 9, less than 8, less than 7.5 or less than 7. In other embodiments, pH of the liquid mixture is between 4 and 9, between 5 and 8, such as between 5.5 and 8.

An appropriate buffer may be selected from acetate, citrate, histidine, maleate, phosphate, succinate, tartrate and TRIS. In one embodiment, the buffer is a phosphate buffer such as $Na/Na_2PO_4$, $Na/K_2PO_4$ or $K/K_2PO_4$.

The buffer can be present in the liquid mixture in an amount of at least 6 mM, at least 10 mM or at least 40 mM. The buffer can be present in the liquid mixture in an amount of less than 100 mM, less than 60 mM or less than 40 mM.

It is well known that for parenteral administration solutions should have a pharmaceutically acceptable osmolality to avoid cell distortion or lysis. A pharmaceutically acceptable osmolality will generally mean that solutions will have an osmolality which is approximately isotonic or mildly hypertonic. Suitably the compositions of the present invention when reconstituted will have an osmolality in the range of 250 to 750 mOsm/kg, for example, the osmolality may be in the range of 250 to 550 mOsm/kg, such as in the range of 280 to 500 mOsm/kg.

Osmolality may be measured according to techniques known in the art, such as by the use of a commercially available osmometer, for example the Advanced® Model 2020 available from Advanced Instruments Inc. (USA).

An "isotonicity agent" is a compound that is physiologically tolerated and imparts a suitable tonicity to a formulation to prevent the net flow of water across cell membranes that are in contact with the formulation. In some embodiments, the isotonicity agent used for the composition is a salt (or mixtures of salts). In other embodiments, however, the composition comprises a non-ionic isotonicity agent and the concentration of sodium chloride in the composition is less than 100 mM, such as less than 80 mM, e.g. less than 50 mM, such as less 40 mM, less than 30 mM and especially less than 20 mM. The ionic strength in the composition may be less than 100 mM, such as less than 80 mM, e.g. less than 50 mM, such as less 40 mM or less than 30 mM.

In a particular embodiment, the non-ionic isotonicity agent is a polyol, such as sorbitol. The concentration of sorbitol may e.g. between about 3% and about 15% (w/v), such as between about 4% and about 10% (w/v). Adjuvants comprising an immunologically active saponin fraction and a TLR4 agonist wherein the isotonicity agent is salt or a polyol have been described in WO2012/080369.

The present invention may be applied for use in the treatment or prophylaxis of a disease or disorder associated with one or more antigens described above. In one embodiment the disease or disorder is selected from malaria, tuberculosis, COPD, HIV and herpes.

To fully obtain the benefits of the present invention, the TLR4 agonist should be administered in a composition which is substantially free of saponin. Suitably the composition comprising the TLR4 agonist will contain less than 1 ug of saponin per human dose, in particular less than 0.5 ug of saponin, especially less than 0.1 ug of saponin (e.g. free of saponin). In certain embodiments, 3D-MPL is provided in a composition which contains less than 1 ug of saponin per human dose, in particular less than 1 ug of saponin, especially less than 0.1 ug of saponin (e.g. free of saponin). In certain embodiments, 3D-MPL is provided in a composition which contain less than 1 ug of QS21 per human dose, in particular less than 0.5 ug of QS21, especially less than 0.1 ug of QS21 (e.g. free of QS21).

Additionally, the saponin should be administered in a composition which is substantially free of TLR4 agonist. Suitably the composition comprising the saponin will contain less than 1 ug of TLR4 agonist per human dose, in particular less than 0.5 ug of TLR4 agonist, especially less than 0.1 ug of TLR4 agonist (e.g. free of TLR4 agonist). In certain embodiments, QS21 is provided in a composition which contains less than 1 ug of TLR4 agonist per human dose, in particular less than 0.5 ug of TLR4 agonist, especially less than 0.1 ug of TLR4 agonist (e.g. free of TLR4 agonist). In certain embodiments, QS21 is provided in a composition which contain less than 1 ug of 3D-MPL per human dose, in particular less than 0.5 ug of 3D-MPL, especially less than 0.1 ug of 3D-MPL (e.g. free of 3D-MPL).

Suitably the compositions used in the present invention do not comprise aluminium salt particles.

Multi-Chamber Syringes

The use of multi-chamber syringes provides a convenient method for the separate administration of the TLR4 agonist and the saponin. Multi-chamber syringes may be configured to provide concurrent but separate delivery of the TLR4 agonist and the saponin, or they may be configured to provide sequential delivery (in either order).

In other configurations, one element may be provided in dry form (e.g., freeze-dried) in one chamber and further reconstituted by diluent contained in the other one before administration.

Examples of multi-chamber syringes may be found in disclosures such as WO2016172396, although a range of other configurations are possible.

The teaching of all references in the present application, including patent applications and granted patents, are herein fully incorporated by reference. A composition or method or process defined as "comprising" certain elements is understood to encompass a composition, method or process (respectively) consisting of those elements. As used herein, 'consisting essentially of' means additional components may be present provided they do not alter the overall properties or function.

The invention will be further described by reference to the following, non-limiting, examples:

Example 1: Investigation of the Impact of Separate TLR4 Agonist and Saponin Formulation on Innate Immune Responses in Mice Objective(s)

The liposomal adjuvant system AS01 induces a specific draining lymph node signature very early after injection. Innate IFNg (i-IFNg) is the IFNg produced by innate draining lymph node cells which in mice peaks around 6 hours after injection with AS01 and results from the synergy between 3D-MPL and QS21 when co-formulated in liposomes. IFNg detected 6 hrs after injection in mice could therefore be a key parameter to discriminate adjuvant system AS01 integrity. The innate signature is thought to be critical for AS01 adjuvant effect. In human sera, the innate IFNg signature is present in patients immunized with an $AS01_B$-adjuvanted vaccine and it is a hallmark of protection (MAL-027).

The aim of this study was to assess if co-formulation of the TLR4 agonist 3D-MPL and saponin QS21 is required to maintain the observed i-IFNg signature. For this, mice were immunized intramuscularly with Varicella Zoster Virus gE antigen adjuvanted with co-formulated 3D-MPL and QS21 or with separate 3D-MPL and QS21 formulated in liposomes. Iliac lymph nodes were collected 6 hours after injection, IFNg content was evaluated by ELISA.

Materials and Methods

Overview of the Study Design

Mice were housed in a pathogen-free facility and the animal studies were conducted under protocols approved by the GSK Committee on Use and Care of Animals.

The mice used in this study were 6-8 week old-females of the C57BL/6 strain, they were separated into 3 groups. Mice were all injected intramuscularly in left and right gastrocnemius muscles. For Group 1 ("Combined" liposomal formulation), each mouse (n=20) received 5 ug of recombinant gE (Haumont et al. 1996; Dendouga et al. 2012; Fochesato et al. 2016) formulated with 1/125 human dose of $AS01_B$, corresponding to 0.4 ug 3D-MPL and 0.4 ug QS21 in a total volume of 40 ul (injected volume per muscle=20 ul, administered using two syringes each with 10 ul). In the group evaluating the "Separate" liposomal formulations (Group 2), each mouse (n=20) received in each muscle (right and left), 1 syringe of 10 ul containing 3D-MPL (0.4 ug 3D-MPL) and gE (1.25 ug) and 1 syringe of 10 ul containing the QS21 (0.4 ug) and gE (1.25 ug). In Group 3 ("Antigen" formulation), each mouse (n=5) received gE antigen in buffer alone (5 ug/animal) in a total volume of 40 ul/animal, administered using four syringes each with 10 ul.

In order to inject with the two syringes at the same site, mice were stained at the injection site. The timing between each injection was kept to a minimum, typically less than 30 seconds.

See Table 1 for a summary of the study design.

TABLE 1

Summary of the study design

| Group | | Injected volume (µl) | Antigen (µg) | MPL (µg) | QS(µg) | |
|---|---|---|---|---|---|---|
| 1 | Per animal | 40 | 5 | 0.4 | 0.4 | |
|   | Per muscle | 20 | 2.5 | 0.2 | 0.2 | |
|   | Per INJS | 10 | 1.25 | 0.1 | 0.1 | Syringe 1 |
|   |   | 10 | 1.25 | 0.1 | 0.1 | Syringe 2 |
| 2 | Per animal | 40 | 5 | 0.4 | 0.4 | |
|   | Per muscle | 20 | 2.5 | 0.2 | 0.2 | |
|   | Per INJS | 10 | 1.25 | 0.2 |   | Syringe 1 |
|   |   | 10 | 1.25 |   | 0.2 | Syringe 2 |
| 3 | Per animal | 40 | 5 |   |   | |
|   | Per muscle | 20 | 2.5 |   |   | |
|   | Per INJS | 10 | 1.25 |   |   | Syringe 1 |
|   |   | 10 | 1.25 |   |   | Syringe 2 |

Immunological Read-Outs

DLN Collection & Sample Processing of Snap Frozen Samples

For the assessment of pro-inflammatory IFNg production, the left and right iliac lymph nodes were collected 6 h after immunization.

Tissue samples dissected from draining lymph were individually homogenized in 1 mL (0.5 mL/dLN) of PBS containing an anti-protease inhibitor cocktail (Sigma-Aldrich). The homogenates were cleared by centrifugation and stored at −70° C. until analysis.

ELISA Mouse IFN-g

The Quantikine Mouse IFN-gamma Immunoassay (R&D systems MIF00) is designed to measure mouse IFNg in mouse serum and tissue homogenate. Results obtained using natural mouse IFNg showed dose-response curves that were parallel to the standard curves obtained using the recombinant kit standards. The complete assay procedure was carefully followed and may be summarised as described below.

A microplate pre-coated with capture antibody is provided. Serum or tissue homogenate samples (or standards) were added. IFNg present in the sample is bound by the immobilized antibody after incubation at room temperature for 2 hours. Unbound materials were washed away (5 washes, with the wash buffer provided). A second HRP-labeled antibody (detection antibody) was added and incubated at room temperature for 2 hours to bind to the captured IFNg. Unbound detection antibody was washed away with another 5 washes. Tetramethylbenzidine (TMB) substrate solution was then added to the wells and incubated at room temperature for 30 minutes (protected from light). Color development was stopped and absorbance of the color at 450 nm was measured (E-Max Reader). Results were calculated using the softmax-pro software.

For the statistical analysis, an analysis of variance model including the group factor was fitted on the log transformed IFNg measures of Groups 1 and 2. Least squares means and the group difference were derived from the model. After back transformation, geometric means with 95% confidence intervals as well as geometric mean ratio were reported.

Results

Figure 2:
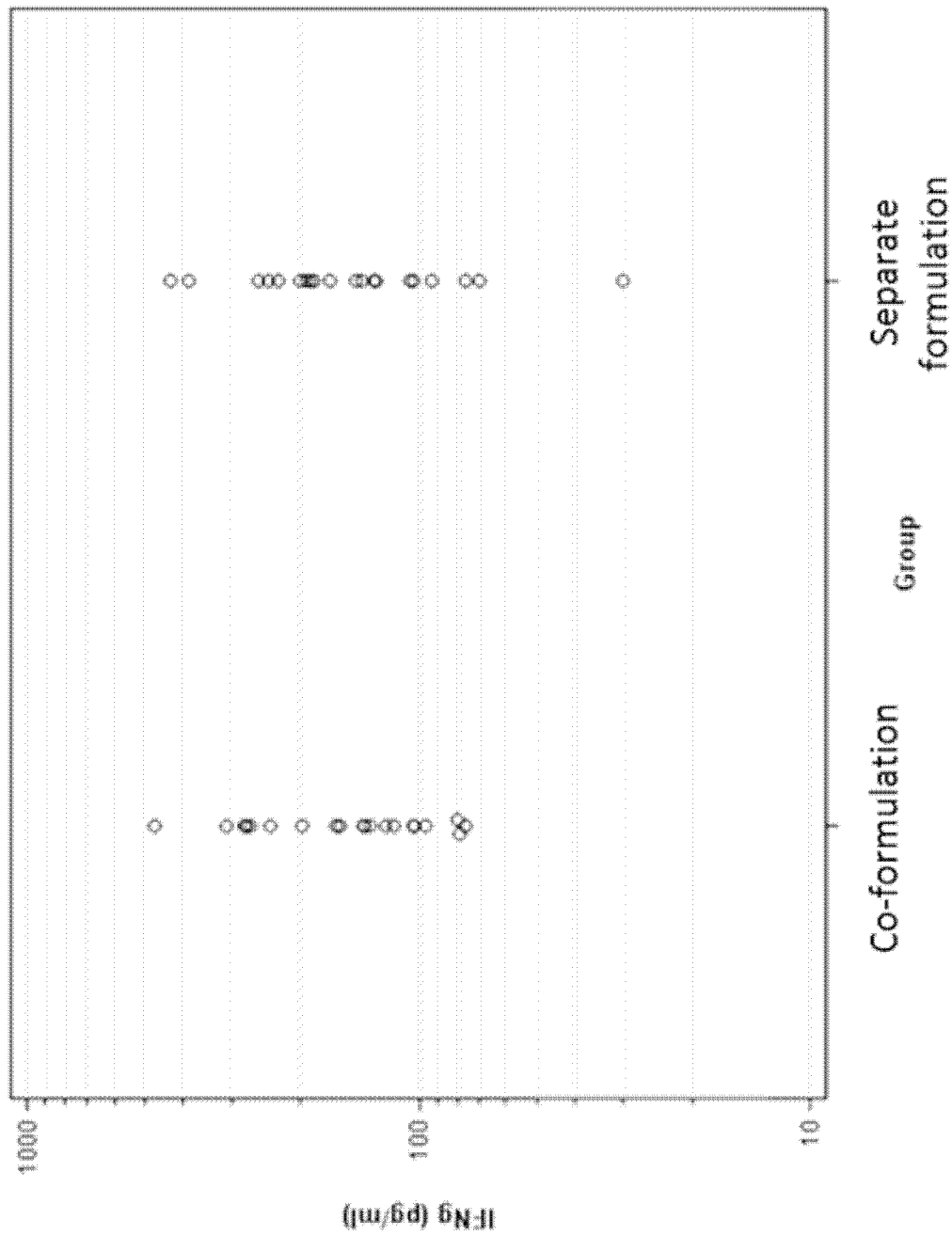
FIG. 2: IFNgamma levels following administration of gE antigen with separate or co-formulated 3D-MPL and QS21 in mice.

The data are graphically represented in FIGS. 1 and 2. The values of the unadjuvanted group were all below the limit of detection. The geometric means estimated for each group are summarised in Table 2. The comparison between co-formulation and separate administration of 3D-MPL and QS21 is summarized in Table 3.

TABLE 2

Geometric means (with 95% confidence interval) of IFNg estimated by the ANOVA model

| Group | Description | Geometric Mean (pg/ml) | 95% CI Lower Bound | 95% CI Upper Bound |
|---|---|---|---|---|
| 1 | Co-formulated | 155.0 | 119.8 | 200.4 |
| 2 | Separated | 149.2 | 115.4 | 192.9 |

TABLE 3

Comparison between the IFNg responses obtained

| Comparison | Geometric Mean Ratio* | 90% Confidence Interval Lower Bound | 90% Confidence Interval Upper Bound |
|---|---|---|---|
| Separate administration vs co-formulation | 0.96 | 0.71 | 1.30 |

*The denominator of the geometric mean ratios is always associated the co-formulation Conclusion It has been demonstrated that separate formulation is non-inferior to co-formulation under the test conditions.

Example 2: Investigation of the Impact of Separate TLR4 Agonist and Saponin Formulation on Adaptive Immune Responses in Mice Objective(s)

In light of the positive finding in Example 1 that innate immune responses observed following administration of separately formulated components were non-inferior to co-formulated components, the work was extended to investigate any impact on adaptive immune responses. For this, mice were immunized intramuscularly with Varicella Zoster Virus gE antigen adjuvanted with co-formulated 3D-MPL and QS21 or with separate 3D-MPL and QS21 at a range of doses. The elicited T cell and antibody responses were then quantified.

Materials and Methods

Overview of the Study Design

Mice were housed in a pathogen-free facility and the animal studies were conducted under protocols approved by the GSK Committee on Use and Care of Animals.

The mice used in this study were 6-8 week old-female of the C57BL/6 strain they were separated into 11 groups of 5 mice. Mice were all injected intramuscularly in left and right gastrocnemius muscles on Day 0 and Day 14. Samples of serum and spleen tissue were taken on Day 21, for measurement of gE specific humoral and T cell (Th1 CD4 and CD8) responses respectively.

TABLE 4

Summary of the study design

| Group | Test material | Formulation approach | Dose of antigen | Dose of each immunostimulant |
|---|---|---|---|---|
| 1 | gE/3D-MPL + QS21 | Co-formulation | 5 ug | 1 ug |
| 2 | | Separate | | |
| 3 | | Co-formulation | | 0.4 ug |
| 4 | | Separate | | |
| 5 | | Co-formulation | | 0.2 ug |
| 6 | | Separate | | |
| 7 | | Co-formulation | | 0.1 ug |
| 8 | | Separate | | |
| 9 | | Co-formulation | | 0.05 ug |
| 10 | | Separate | | |
| 11 | gE/PBS | | — | — |

For each group, a total volume of 20 ul was administered on each occasion. This consisted of 2 injections into the left muscle of either separate formulations (for split 3D-MPL and QS21) or identical formulations (co-formulated and control PBS). In order to inject with the two syringes at the same site, mice were stained at the injection site. The timing between the two injections was kept to a minimum, less than 30 seconds.

Immunological Read-Outs

Spleen Collection & Sample Processing for Cell Suspension and Intracellular Cytokine Staining (ICS) at Day 7PII Spleens were collected in RPMI medium and dissociated using a potter tissue grinder (homogenizer) using two up and down strokes. Homogenized samples were transferred to 15 ml round-bottom polypropylene tubes. Fibrous material was removed by filtration through a 100 um nylon cell strainer. Cells were then washed, counted and re-suspended at 10*7 cells per ml.

ICS (Intracellular Cytokine Staining) is the technology which allows the quantification of antigen specific T lymphocytes on the basis of cytokine production.

Lymphoid cells are re-stimulated O.N. in vitro with gE peptides in the presence of a secretion inhibitor (brefeldin A). These cells are then processed by conventional immunofluorescent procedure using fluorescent antibodies (extracellular staining: CD4, CD8, intracellular staining: TNFa, IFNg and IL2). Results are expressed as a frequency of cytokine positive cell within CD4 and CD8 T-cell population. The analysis was focused on cells expressing at least two cytokines.

ELISA gE at Day 7PII on Sera

Anti-gE (VZV) total IgG were measured by ELISA. 96 well-plates were coated with antigen overnight at 4° C. The plates were then washed and saturated with saturation buffer for 1 hour at 37° C. After, 100 ul of diluted mouse serum or standard or control was added and incubated for 1 hour at 37° C. After wash, the plates were incubated for 1 hour at 37° C. with 100 ul anti mouse IgG-HRP. After washing, 100 ul of TMB per well was added and the plates were kept in the dark at room temperature for 15 minutes. To stop the reaction, 100 ul of $H_2SO_4$ 0.4N was added per well. The absorbance was read at a wavelength of 450/630 nm by an Elisa plate reader. Results were calculated using the Softmax-pro software.

Results

1. T Cell Response: gE Specific CD4+ T Cell Responses

Figure 3:
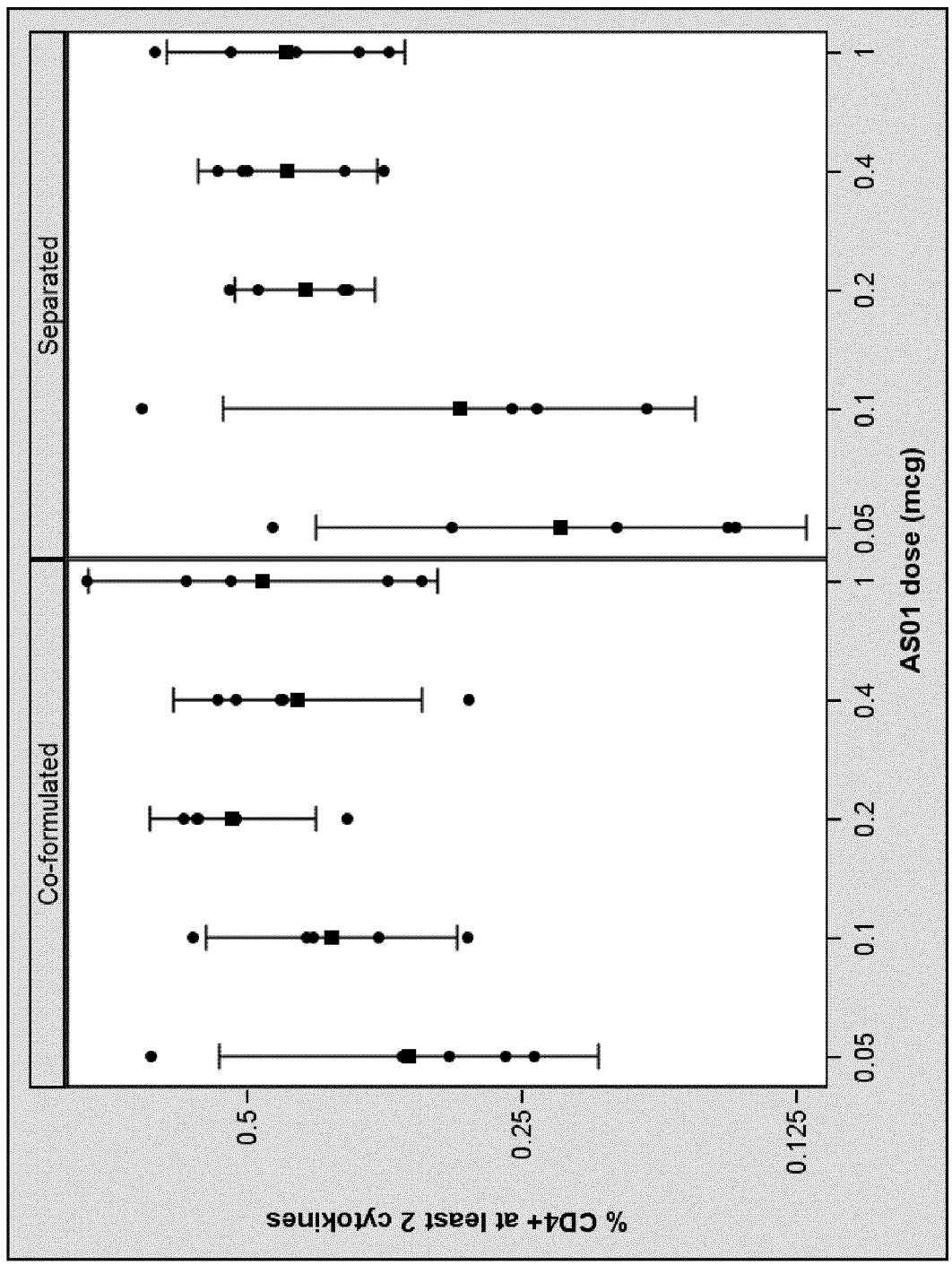
FIG. 3: CD4 T cell responses following separate administration of gE antigen and separate or co-formulated 3D-MPL and QS21 in mice.
Figure 4:
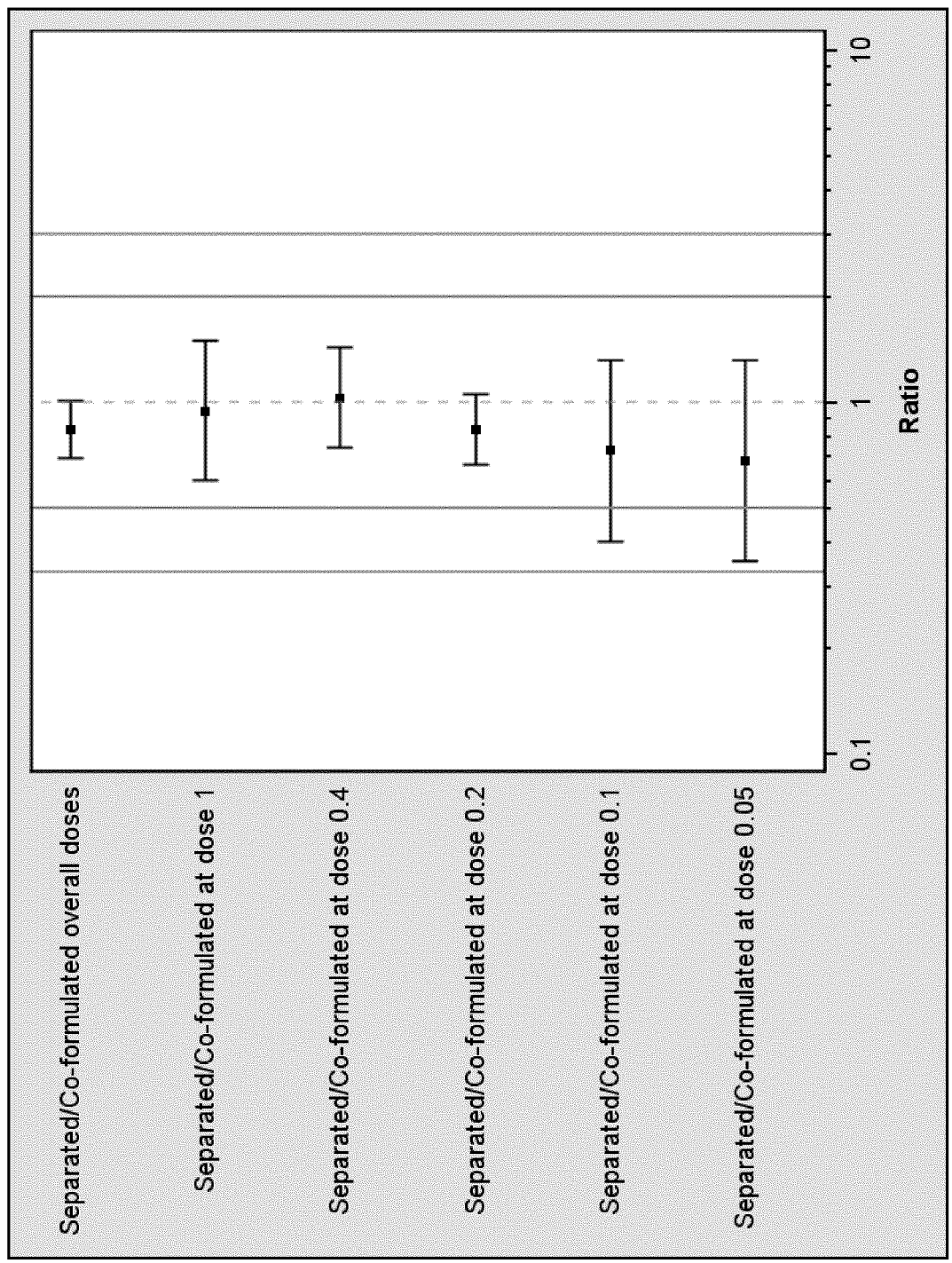
FIG. 4: Ratio of CD4 T cell responses following administration of gE antigen and separate or co-formulated 3D-MPL and QS21 in mice.

The data are graphically represented in FIGS. 3 and 4, The geometric means of each group are summarised in Table 5. The comparisons of co-formulation versus separate formulation are summarised in Table 6.

TABLE 5

CD4+ expressing at least 2 cytokines: Geometric means and their 95% CIs by group

| Process | Dose | N | Geometric Mean | 95% CI-Lower Limit | 95% CI-Upper Limit |
|---|---|---|---|---|---|
| Co-formulated | 0.05 | 5 | 0.33 | 0.21 | 0.54 |
| Co-formulated | 0.1 | 5 | 0.40 | 0.29 | 0.56 |
| Co-formulated | 0.2 | 5 | 0.52 | 0.42 | 0.64 |
| Co-formulated | 0.4 | 5 | 0.44 | 0.32 | 0.60 |
| Co-formulated | 1 | 5 | 0.48 | 0.31 | 0.75 |
| Separated | 0.05 | 5 | 0.23 | 0.12 | 0.42 |
| Separated | 0.1 | 5 | 0.29 | 0.16 | 0.53 |
| Separated | 0.2 | 5 | 0.43 | 0.36 | 0.52 |
| Separated | 0.4 | 5 | 0.45 | 0.36 | 0.57 |
| Separated | 1 | 5 | 0.45 | 0.34 | 0.61 |

TABLE 6

CD4+ expressing at least 2 cytokines: Geometric mean ratios and their 95% Cs (comparison of formulation dose by dose)

| Comparison | Geometric Mean Ratio | 95% CI-Lower Limit | 95% CI-Upper Limit |
|---|---|---|---|
| Separated/Co-formulated at dose 0.05 | 0.68 | 0.35 | 1.31 |
| Separated/Co-formulated at dose 0.1 | 0.72 | 0.40 | 1.31 |
| Separated/Co-formulated at dose 0.2 | 0.83 | 0.66 | 1.05 |
| Separated/Co-formulated at dose 0.4 | 1.03 | 0.74 | 1.42 |
| Separated/Co-formulated at dose 1 | 0.94 | 0.60 | 1.48 |

In this experiment gE specific CD4+ T cell frequencies increase with the dose of immunostimulant until the dose of 0.2 ug (1/250HD per animal) then reaching a plateau. This was observed for both the separate and the co-formulations (see Table 6). Moreover, when looking at the geometric mean ratio separated/co-formulated of CD4+ T cell frequencies, the two formulation approaches induce comparable responses at the dose of 1, 0.4, and 0.2 ug. A slight difference appears with the lowest doses (0.1 and 0.05 ug) (see Table 6).

2. Antibody Response: Anti-gE IgG Level

Figure 5:
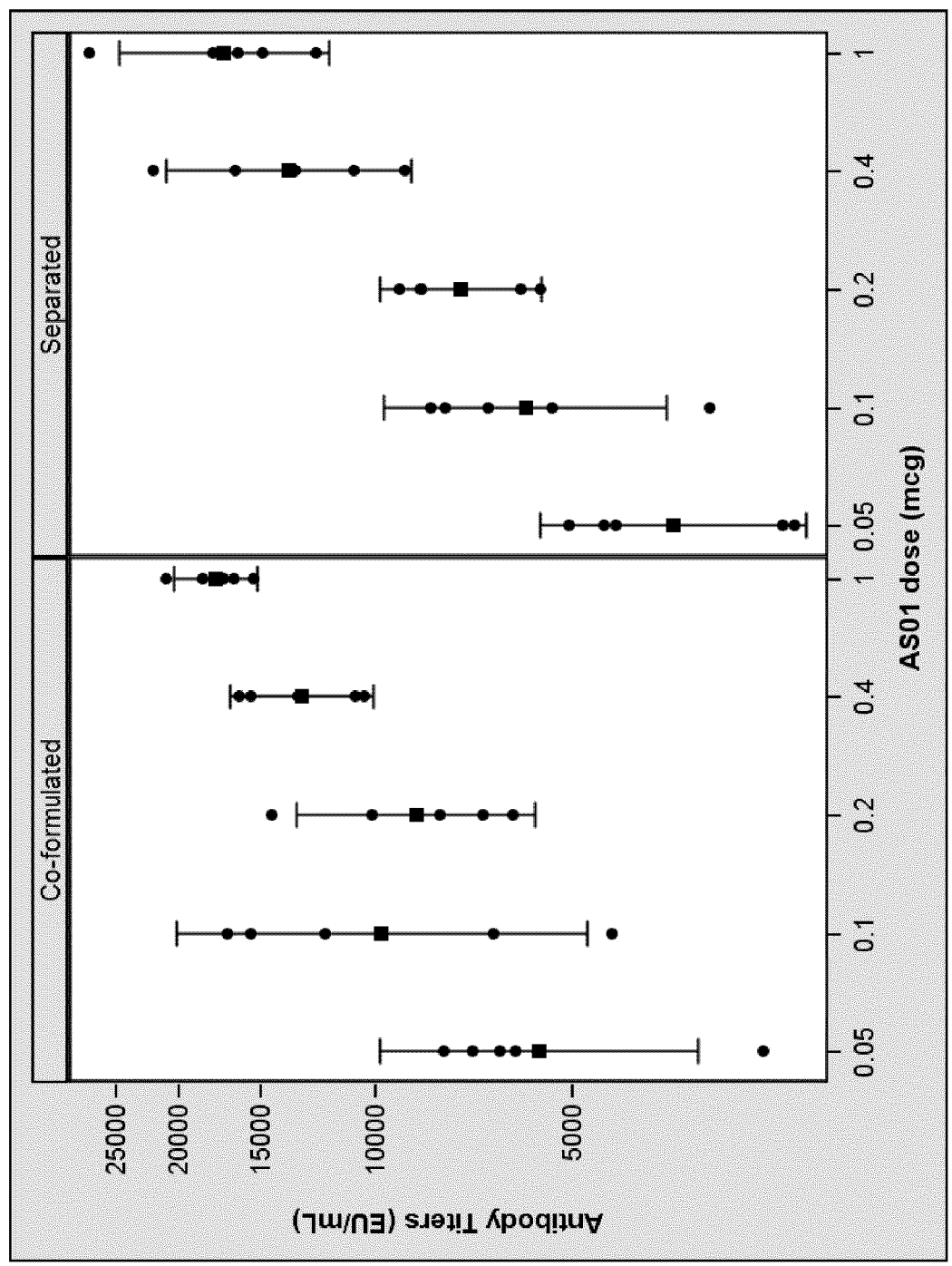
FIG. 5: Antibody responses following administration of gE antigen and separate or co-formulated 3D-MPL and QS21 in mice.
Figure 6:
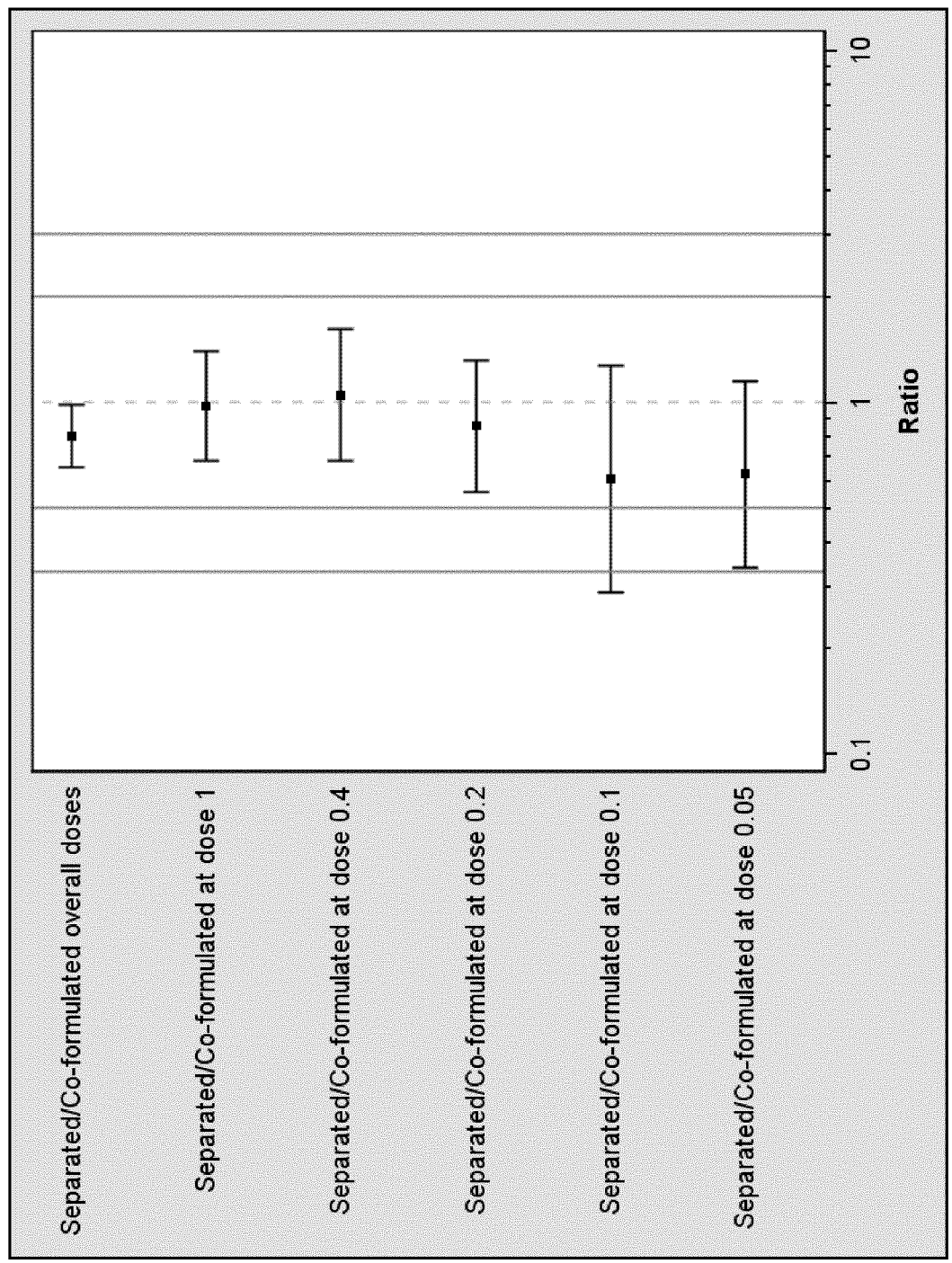
FIG. 6: Ratio of antibody responses following administration of gE antigen and separate or co-formulated 3D-MPL and QS21 in mice.

The data are graphically represented in FIGS. 5 and 6. The geometric means of each group are summarised in Table 7. The comparisons of co-formulation versus separate formulation are summarised in Table 8.

TABLE 7

Antibody response: Geometric means and their 95% CIs by group

| Process | Dose | N | Geometric Mean | 95% CI-Lower Limit | 95% CI-Upper Limit |
|---|---|---|---|---|---|
| Co-formulated | 0.05 | 5 | 5642.86 | 3223.63 | 9877.64 |
| Co-formulated | 0.1 | 5 | 9824.45 | 4768.72 | 20240.18 |
| Co-formulated | 0.2 | 5 | 8708.63 | 5712.27 | 13276.73 |
| Co-formulated | 0.4 | 5 | 13041.60 | 10126.89 | 16795.23 |
| Co-formulated | 1 | 5 | 17620.54 | 15231.37 | 20384.46 |
| Separated | 0.05 | 5 | 3514.16 | 2200.79 | 5611.32 |
| Separated | 0.1 | 5 | 5920.71 | 3603.14 | 9728.96 |
| Separated | 0.2 | 5 | 7436.33 | 5600.54 | 9873.86 |
| Separated | 0.4 | 5 | 13624.91 | 8850.08 | 20975.86 |
| Separated | 1 | 5 | 17129.23 | 11845.40 | 24770.00 |

TABLE 8

Antibody response: Geometric mean ratios and their 95% Cis (comparison of formulation dose by dose)

| Comparison | Geometric Mean Ratio | 95% CI-Lower Limit | 95% CI-Upper Limit |
|---|---|---|---|
| Separated/Co-formulated at dose 0.05 | 0.62 | 0.34 | 1.15 |
| Separated/Co-formulated at dose 0.1 | 0.60 | 0.29 | 1.27 |
| Separated/Co-formulated at dose 0.2 | 0.85 | 0.55 | 1.32 |
| Separated/Co-formulated at dose 0.4 | 1.04 | 0.68 | 1.61 |
| Separated/Co-formulated at dose 1 | 0.97 | 0.68 | 1.40 |

The results suggest that gE specific IgG level increase with the dose of immunostimulants. This was observed for both the separated and the co-formulated administrations (see Table 8). Moreover, when looking at the geometric mean ratio separated/co-formulated IgG levels, it seems that the two formulations induce similar antibody response at the dose of 1, 0.4 and 0.2 ug. A slight difference appears with the lowest doses (0.1 and 0.05 ug) (see Table 9).

Conclusion

Overall, separate administration of TLR4 agonist and saponin did not result in a substantial change in the observed cellular and antibody responses.

BIBLIOGRAPHY

Arias M A et al. (2012) Glucopyranosyl Lipid Adjuvant (GLA), a Synthetic TLR4 Agonist, Promotes Potent Systemic and Mucosal Responses to Intranasal Immunization with HIVgp140. PLoS ONE 7(7): e41144. doi:10.1371/journal.pone.0041144.

Black, S., E. De Gregorio, and R. Rappuoli. 2015. Developing vaccines for an aging population. Science translational medicine. 7:281ps288.

Coccia et al. (2017) Cellular and molecular synergy in AS01-adjuvanted vaccines results in an early IFNγ response promoting vaccine immunogenicity. npj Vaccines 2, Article number: 25 doi:10.1038/s41541-017-0027-3

Coler R N et al. (2011) Development and Characterization of Synthetic Glucopyranosyl Lipid Adjuvant System as a Vaccine Adjuvant. PLoS ONE 6(1): e16333. doi:10.1371/journal.pone.0016333.

Dalsgaard et al. in 1974 ("Saponin adjuvants", Archiv. für die gesamte Virusforschung, Vol. 44, Springer Verlag, Berlin, p 243-254).

De Becker, G., V. Moulin, B. Pajak, C. Bruck, M. Francotte, C. Thiriart, J. Urbain, and M. Moser. 2000. The adjuvant monophosphoryl lipid A increases the function of antigen-presenting cells. International immunology. 12:807-815.

Dendouga, N., M. Fochesato, L. Lockman, S. Mossman, and S. L. Giannini. 2012. Cell-mediated immune responses to a varicella-zoster virus glycoprotein E vaccine using both a TLR agonist and QS21 in mice. Vaccine. 30:3126-3135.

Didierlaurent A. M., Collignon C., Bourguignon P., Wouters S., Fierens K., Fochesato M., Dendouga N., Langlet C., Malissen B., Lambrecht B. N., Garcon N., Van Mechelen M., and S. Morel. 2014. Enhancement of Adaptive Immunity by the Human Vaccine Adjuvant AS01 Depends on Activated Dendritic Cells. The Journal of Immunology. 193.

Dillon, D. C., M. R. Alderson, C. H. Day, D. M. Lewinsohn, R. Coler, T. Bement, A. Campos-Neto, Y. A. W. Skeiky, I. M. Orme, A. Roberts, S. Steen, W. Dalemans, R. Badaro, S. G. Reed. 1999. Molecular characterization and human T-cell responses to a member of a novel *Mycobacterium tuberculosis* mtb39 gene family. *Infection and Immunity.* 67(6):2941-2950.

Garcon, N., and M. Van Mechelen. 2011. Recent clinical experience with vaccines using MPL- and QS-21-containing adjuvant systems. *Expert review of vaccines.* 10:471-486.

Fochesato, M., Dendouga N. and Boxus M. 2016 *Hum Vaccin Immunother* 12(8):2092-2095.

Haumont M., Jacquet A., Massaer M., Deleersnyder V., Mazzu P., Bollen A. and Jacobs P 1996 Purification, characterization and immunogenicity of recombinant varicella-zoster virus glycoprotein gE secreted by Chinese hamster ovary cells *Virus Res* 1996 40(2):199-204.

Helminen M. E., I. Maciver, J. L. Latimer, L. D. Cope, G. H. McCracken Jr, and E. J. Hansen. 1993. A major outer membrane protein of *Moraxella catarrhalis* is a target for antibodies that enhance pulmonary clearance of the pathogen in an animal model. *Infection and Immunity.* 61:2003-2010.

Ismaili, J., J. Rennesson, E. Aksoy, J. Vekemans, B. Vincart, Z. Amraoui, F. Van Laethem, M. Goldman, and P. M. Dubois. 2002. Monophosphoryl lipid A activates both human dendritic cells and T cells. *Journal of immunology.* 168:926-932.

Kensil, C. R., U. Patel, M. Lennick, and D. Marciani. 1991. Separation and characterization of saponins with adjuvant activity from *Quillaja saponaria* Molina cortex. *Journal of immunology.* 146:431-437.

Kensil, C. R., and R. Kammer. 1998. QS-21: a water-soluble triterpene glycoside adjuvant. *Expert opinion on investigational drugs.* 7:1475-1482.

Lambrecht, B. N., M. Kool, M. A. Willart, and H. Hammad. 2009. Mechanism of action of clinically approved adjuvants. *Current opinion in immunology.* 21:23-29.

Leroux-Roels, I., G. Leroux-Roels, F. Clement, P. Vandepapeliere, V. Vassilev, E. Ledent and T. C. Heineman. 2012. A Phase 1/2 Clinical Trial Evaluating Safety and Immunogenicity of a Varicella Zoster Glycoprotein E Subunit Vaccine Candidate in Young and Older Adults. *Journal of Infectious. Diseases.,* 206:1280-1290.

Li, H., S. B. Willingham, J. P. Ting, and F. Re. 2008. Cutting edge: inflammasome activation by alum and alum's adjuvant effect are mediated by NLRP3. *Journal of immunology.* 181:17-21.

Livingston, P. O., S. Adluri, F. Helling, T. J. Yao, C. R. Kensil, M. J. Newman, and D. Marciani. 1994. Phase 1 trial of immunological adjuvant QS-21 with a GM2 ganglioside-keyhole limpet haemocyanin conjugate vaccine in patients with malignant melanoma. *Vaccine.* 12:1275-1280.

Ragupathi, G., J. R. Gardner, P. O. Livingston, and D. Y. Gin. 2011. Natural and synthetic saponin adjuvant QS-21 for vaccines against cancer. *Expert review of vaccines.* 10:463-470

Rigter, A., I. Widjaja, H. Versantvoort, F. E. J. Coenjaerts, M. van Roosmalen, K. Leenhouts, P. J. M. Rottier, B. J. Haijema, C. A. M. de Haan. 2013. A Protective and Safe Intranasal RSV Vaccine Based on a Recombinant Prefusion-Like Form of the F Protein Bound to Bacterium-Like Particles. *PLOS One.* 8:e71072.

Martin, M., S. M. Michalek, and J. Katz. 2003. Role of innate immune factors in the adjuvant activity of monophosphoryl lipid A. *Infection and immunity.* 71:2498-2507.

Marty-Roix, R. et al. Identification of QS-21 as an Inflammasome-activating Molecular Component of Saponin Adjuvants. *J. Biol. Chem.* 291, 1123-36 (2016)

Mata-Haro, V., C. Cekic, M. Martin, P. M. Chilton, C. R. Casella, and T. C. Mitchell. 2007. The vaccine adjuvant monophosphoryl lipid A as a TRIF-biased agonist of TLR4. *Science.* 316:1628-1632.

McLellan, J. S., M. Chen, S. Leung, K. W. Graepel, X. Du, Y. Yang, T. Zhou, U. Baxa, E. Yasuda, T. Beaumont, A. Kumar, K. Modjarrad, Z. Zheng, M. Zhao, N. Xia, P. D. Kwong, and B. S. Graham. 2013. Structure of RSV Fusion Glycoprotein Trimer Bound to a Prefusion-Specific Neutralizing Antibody. *Science.* 340:1113-1117.

McLellan, J. S., M. Chen, M. G. Joyce, M. Sastry, G. B. E. Stewart-Jones, Y. Yang, B. Zhang, L. Chen, S. Srivatsan, A. Zheng, T. Zhou, K. W. Graepel, A. Kumar, S. Moin, J. C. Boyington, G.-Y. Chuang, C. Soto, U. Baxa, A. Q. Bakker, H. Spits, T. Beaumont, Z. Zheng, N. Xia, S-Y. Ko, J-P. Todd, S. Rao, B. S. Graham, and P. D. Kwong. 2013. Structure-Based Design of a Fusion Glycoprotein Vaccine for Respiratory Syncytial Virus. *Science.* 342:592-598.

Newman, M. J., J. Y. Wu, B. H. Gardner, K. J. Munroe, D. Leombruno, J. Recchia, C. R. Kensil, and R. T. Coughlin. 1992. Saponin adjuvant induction of ovalbumin-specific CD8+ cytotoxic T lymphocyte responses. *Journal of immunology.* 148:2357-2362.

Skeiky, Y. A. W., M. J. Lodes, J. A. Guderian, R. Mohamath, T. Bement, M. R. Alderson, and S. G. Reed. 1999. Cloning, expression, and immunological evaluation of two putative secreted serine protease antigens of *Mycobacterium tuberculosis. Infection and Immunity.* 67(8): 3998-4007.

Skeiky, Y. A. W., M. R. Alderson, P. J. Ovendale, J. A. Guderian, L. Brandt, D. C. Dillon, A. Campos-Neto, Y. Lobet, W. Dalemans, I. M. Orme, and S. G. Reed. 2004. Differential immune responses and protective efficacy induced by components of a tuberculosis polyprotein vaccine, Mtb72F, delivered as naked DNA or recombinant protein. *Journal of immunology.* 172:7618-7628.

Soltysik, S., J. Y. Wu, J. Recchia, D. A. Wheeler, M. J. Newman, R. T. Coughlin, and C. R. Kensil. 1995. Structure/function studies of QS-21 adjuvant: assessment of triterpene aldehyde and glucuronic acid roles in adjuvant function. *Vaccine.* 13:1403-1410.

Vafai A., 1994. Antibody binding sites on truncated forms of varicalla-zoster virus gp1(gE) glycoprotein, *Vaccine.* 12:1265-9.

The invention claimed is:

1. A method for adjuvanting the immune response of a subject to an antigen using 3-de-O-acylated monophosphoryl lipid A and QS21, said method comprising the steps:
   (i) administering to the subject the 3-de-O-acylated monophosphoryl lipid A;
   (ii) administering to the subject the QS21;
   (iii) administering to the subject the antigen;
wherein the steps can be undertaken in any order, the 3-de-O-acylated monophosphoryl lipid A and the QS21 are administered separately, and antigen may optionally be co-formulated with the 3-de-O-acylated monophosphoryl lipid A, the QS21 or co-formulated with each of the 3-de-O-acylated monophosphoryl lipid A and QS21 and wherein the 3-de-O-acylated monophosphoryl lipid A, QS21 and antigen are all administered within 6 hours.

2. The method of claim 1, wherein the amount of 3-de-O-acylated monophosphoryl lipid A in a single adult human dose is 1 to 100 ug and the amount of QS21 in a single adult human dose is 1 to 100 ug.

3. The method of claim 1, wherein the 3-de-O-acylated monophosphoryl lipid A and QS21 are administered to locations less than 10 cm apart.

4. The method of claim 1, wherein the 3-de-O-acylated monophosphoryl lipid A and QS21 are administered to a location draining to the same lymph node.

5. The method of claim 1, wherein the 3-de-O-acylated monophosphoryl lipid A is formulated with liposomes and the QS21 is formulated with liposomes.

6. The method of claim 1, wherein an antigen is co-formulated with the 3-de-O-acylated monophosphoryl lipid A and/or an antigen is co-formulated with the QS21.

7. The method of claim 1, wherein the antigen is derived from a human or non-human pathogen including or from a cancer cell or tumor cell.

8. The method of claim 4, wherein the subject is a human.

9. The method of claim 6, wherein the amount of 3-de-O-acylated monophosphoryl lipid A in a single adult human dose is 1 to 100 ug and the amount of QS21 in a single adult human dose is 1 to 100 ug.

10. The method of claim 9, wherein the 3-de-O-acylated monophosphoryl lipid A is formulated with liposomes and the QS21 is formulated with liposomes.

* * * * *